US006075119A

United States Patent [19]
Bannan et al.

[11] Patent Number: 6,075,119
[45] Date of Patent: Jun. 13, 2000

[54] PEPTIDES USEFUL FOR REDUCING SYMPTOMS OF TOXIC SHOCK SYNDROME

[75] Inventors: Jason D. Bannan, Thompson Station, Tenn.; John B. Zabriskie, New York, N.Y.

[73] Assignee: The Rockefeller University, New York, N.Y.

[21] Appl. No.: 08/838,413

[22] Filed: Apr. 7, 1997

[51] Int. Cl.[7] .................. A61K 39/395; A61K 39/00; A61K 38/00; C07K 5/00

[52] U.S. Cl. .................. 530/300; 530/350; 530/324; 530/325; 530/326; 530/327; 530/328; 530/333; 424/185.1; 424/192.1; 424/244.1; 424/243.1; 424/130.1

[58] Field of Search .................. 530/350, 300, 530/324, 325, 326, 327, 328, 333; 424/184.1, 185.1, 192.1, 244.1, 243.1, 130.1

[56] References Cited

U.S. PATENT DOCUMENTS

| | | |
|---|---|---|
| 5,378,607 | 1/1995 | Chelladurai et al. . |
| 5,437,978 | 8/1995 | Ubukata et al. . |
| 5,470,716 | 11/1995 | Leung et al. . |
| 5,476,767 | 12/1995 | Leung et al. . |
| 5,519,114 | 5/1996 | Johnson et al. . |
| 5,529,934 | 6/1996 | Chelladurai et al. . |
| 5,545,716 | 8/1996 | Johnson et al. . |
| 5,585,465 | 12/1996 | Leung et al. . |
| 5,601,830 | 2/1997 | Su et al. . |
| 5,705,151 | 1/1998 | Dow et al. . |
| 5,728,388 | 3/1998 | Terman . |

FOREIGN PATENT DOCUMENTS

| | | |
|---|---|---|
| WO 91/10680 | 7/1991 | WIPO . |
| WO 93/24136 | 12/1993 | WIPO . |
| WO 94/20124 | 9/1994 | WIPO . |
| WO 94/25483 | 11/1994 | WIPO . |
| WO 96/36366 | 11/1996 | WIPO . |
| WO 96/40930 | 12/1996 | WIPO . |

OTHER PUBLICATIONS

Van Den Bussche, R.A. et al., "Molecular Evolution of the Staphylococcal and Streptococcal Pyrogenic Toxin Gene Family", *Molecular Phylogenetics and Evolution*, 2:281–292, (Dec. 1993).

Copy of Search Report (listing references and related patents).

Reda et al Infection & Immunity. 62/5:1867–74, 1994.

Fischetti et al, J. Exp. Med. 144/1:32–53, 1976.

Bavari, S. et al., "Superantigen vaccines: a comparative study of genetically attenuated receptor–binding mutants of Staphylococcal enterotoxin A", *Journal of Infectious Diseases* 174(2):338–45 (1996).

Blomster–Hautamaa, E.A. et al. "Localization of biologic functions of toxic shock syndrome toxin–1 by use of monoclonal antibodies and cyanogen bromide–generated toxin fragments," *J. Immunol.* 137(11):3572–3576 (1986).

Bohach, G.A., et al., "Biological and immunological properties of the carboxyl terminus of Staphylococcal entero––toxin C1," *Infect. Immun.* 27(1):23–28 (1989).

Bonventre, P.F. et al., "A mutation at histidine residue 135 of toxic shock syndrome toxin yields an immunogenic protein with minimal toxicity," *Infect. Immun.* 63(2):509–515 (1995).

Chu, N.R. et al., "Comparison of peptide and superantigen––induced anergy in a peptide–specific polyclonal human T cell line," *Int. Immunol.* 7(7):1057–1063 (1995).

Drynda, A., et al., "Role of a carboxy–terminal site of toxic shock syndrome toxin 1 in eliciting immune responses of human peripheral blood mononuclear cells," *Infect. Immun.* 63(3):1095–1101 (1995).

Edwin, C., et al., "Structure–activity relationship of toxic––shock–syndrome toxin–1: derivation and characterization of immunologically and biologically active fragments," *J. Infect. Dis.* 158(6):1287–1295 (1988).

Edwin, C., et al., "Specificity and cross–reactivity of staphylococcal enterotoxin A monoclonal antibodies with enterotoxins, B, $C_1$, D, and E", *Applied & Environmental Microbiology*, 52(6): 1253–7 (1986).

Griggs, N.D., et al., "Mapping of Multiple Binding Domains of the Superantigen Staphylococcal Enterotoxin A for HLA", *J. Immunol.*, 148(8):2516–2521 (1992).

Grossman, D., et al., "Mutation of the disulfide loop in staphylococcal enterotoxin–A –Consequences for T–Cell recognition," *J. Immunol.* 147(10):3274–3281 (1991).

Harris, T.O. and Betley, M.J., "Biological activities of Staphylococcal enterotoxin–type–A mutants with N–terminal substitutions," *Infect. Immun.* 63(6):2133–2140 (1995).

Hartwig, U.F., et al., "Mutations affecting MHC class II binding of the superantigen streptococcal erythrogenic toxin A", *Intern'l Immunol.*, 5:869–75 (1993).

Hayball, J.D., et al., "The domain structure and functional relationships in the bacterial superantigen SEB," *Biol. Chem. Hoppe–Seyler* 376:303–309 (1995).

(List continued on next page.)

*Primary Examiner*—Nita Minnifield
*Attorney, Agent, or Firm*—Morgan & Finnegan, LLP

[57] ABSTRACT

This invention relates to compositions and methods for eliciting an immunogenic response in mammals, including responses which provide protection against, or reduce the severity, of toxic shock from bacterial infections. More particularly it relates to peptides derived from homologous sequences of the family of staphylococcal and streptococcal toxins, which may be polymeric, and carrier-conjugates thereof, and their use to induce serum antibodies. The invention also relates to serum antibodies induced by the peptides and carrier-conjugates and their use to prevent, treat, or protect against the toxic effects of most, if not all, of the staphylococcal and streptococcal toxins.

The invention also relates to diagnostic assays and kits to detect the presence of staphylococcal and streptococcal toxins, or antibodies thereto. The invention also relates isolated and purified to nucleic acids encoding the peptides of the invention and transformed host cells containing those nucleic acids.

25 Claims, 4 Drawing Sheets

OTHER PUBLICATIONS

Hoffmann, M.L., et al., "Predictions of T–Cell Receptor– and Major Histocompatibility Complex–Binding Sites on Staphylococcal Enterotoxin C1", *Infect. Immun.*, 62(8):3396–3407 (1994).

Hovde, C.J., et al. "Investigation of the role of disulphide bond activity and structure of staphylococcal entertoxin C1," *Mol. Micro.* 13(5):897–909 (1994).

Huang, I.Y., et al., "Complete amino acid sequence of staphylococcal enterotoxin A", *J. Biol. Chem.*, 262(15) 7006–7013 (1987).

Huang, I.Y., et al., "The primary structure of staphylococcal enterotoxin B. III. The cyanogen bromide peptides of reduced and aminoethylated entertoxin B, and the complete amino acid sequence", *J. Biol. Chem.*, 245(14):3518–25 (1970).

Hynes, W. L., et al. "Immunologic Cross–Reactivity of Type A Streptococcal Exotoxin (Erythrogenic Toxin) and Staphylococcal Enterotoxins B and C1", *Infect. Immun.*, 55(3): 837–838 (1987).

Iandolo, J.J., "Genetic analysis of extracellular toxins of *Staphylococcus aureus*", *Annu. Rev. Microbiol.*, 43:375–402 (1989).

Jett, M., et al., "Identification of Staphylococcal Enterotoxin B Sequences Important for Induction of Lymphocyte Proliferation by Using Synthetic Peptide Fragments of the Toxin", *Infect. Immun.*, 62(8):3408–3415 (1994).

Kline, J.B. and Collins, J.M., "Analysis of superantigenic activity of mutant and allelic forms of streptococcal pyrogenic exotoxin A," *Infect. Immun.* 64(3):861–869 (Mar. 1996).

Lamphear, J.G., et al., "Residues near the amino and carboxyl termini of staphylococcal enterotoxin E independently mediate TCR V beta–specific interactions", *J. Immunol.*, 156(6):2178–85 (1996).

Marrack, P., et al. "The Staphylococcal Enterotoxins and Their Relatives", *Science*, vol. 248, pp. 705–711 (1990).

Norrby–Teglund, A., et al., "Plasma from patients with severe invasive group A streptococcal infections treated with normal polyspecific IgG inhibits streptococcal superantigen– –induced T cell proliferation and cytokine production", *J. Immunol.*, 156(8):3057–64 (1996).

Pontzer, C.H., et al., "Localization Of An Immune Functional Site On Staphylococcal Enterotoxin A Using The Synthetic Peptide Approach", *J. Immunol.*, 143(1):280–284 (1989).

Pontzer, C.H., et al., "Agonist Properties of a Microbial Superantigen Peptide", *Biochem. Biophys. Res. Comm.*, 193(3):1191–1197 (1993).

Printout from the Genetics Computer Group "Motifs" software (citing: Program Manual for the Wisconsin Package, Version 8, Sep. 1994, Genetics Computer Group, 575 Science Drive, Madison, WI, USA 53711).

Ramesh, N., et al., "A toxic shock syndrome toxin–1 peptide that shows homology to mycobacterial heat shock protein 18 is presented as conventional antigen to T cells by multiple HLA–DR alleles," *J. Immunol.* 148(4):1025–1030 (1992).

Ramesh, N., et al., "A toxic shock syndrome toxin–1 peptide that shows homology to amino acids 180–193 of mycobacterial heat shock protein 65 is presented as conventional antigen," *Immunol. Invest.* 23(6–7):381–391 (1994).

Schlievert, P.M., et al., "Molecular structure of staphylococcus and streptococus superantigens", *J. Clin. Immunol.*, 15(6) Suppl:4S–10S (1995).

Singh, B.R., et al., "Comparative structural analysis of staphylococcal enterotoxins A and E", *J. Biol. Chem.*, 264(8):4404–11 (1989).

Singh, B.R. et al., Structural analysis of staphylococcal enterotoxins B and $C_1$ using circular dichroism and fluorescence spectroscopy', *Biochemistry*, 27(24):8735–41 (1988).

Soos, J.M. and Johnson, H.M., "Multiple binding sites on the superantigen, staphyloccal enterotoxin B, imparts versatility in binding to MHC Class II molecules," *Biochem. Biophys. Res. Comm.* 201(2):596–602 (1994).

Spero, L., et al. "Biological Activities of the Peptides of Staphylococcal Enterotoxin C Formed by Limited Tryptic Hydrolysis", *J. Biol. Chem.*, 253(24):8787–8791 (1978).

Spero, L., et al., "On the cross–reactivity of staphylococcal enterotoxins A, B, and C", *J. Immunol.*, 120:86–89 (1978).

Spero, L., et al., "Cross–reaction between tryptic polypeptides of staphylococcal enterotoxins B and C", *J. Immunol.*, 122:1285–1289 (1979).

Sriskandan, S. et al., "Streptococcal pyrogenic exotoxin A release, distribution, and role in a murine model of fascitis and multiorgan failure due to *Streptococcus pyogenes*", *J. Infect. Dis.*, 173(6):1399–407 (1996).

Swaminathan, S., et al. "Crystal structure of staphylococcal enterotoxin B, a superantigen", *Nature*, 359:801–806 (1992).

Takei, S., et al. "Intravenous immunoglobulin contains specific antibodies inhibitory to activation of T cells by staphylococcal toxin superantigens", *J. Clin. Invest.*, 91:602–607 (1993).

Warren, J.R., et al. "Stabilization of native structure by the closed disulfide loop of staphyloccal enterotoxin B," *Biochemica et Biophysica Acta* 359:351–363 (1974).

Woo, J., et al. "Development of mutants of Staphylococcal toxic shock syndrome toxin–1," *Molecules and Cells*, 6(1):79–85 (Feb. 1996).

Oral presentation by Dr. Jason Bannan at "XIII Lancefield International Symposium on Streptococci and Streptococcal Diseases, Paris, France, Sep. 16, 1996 to Sep. 20, 1996".

Bannan, J.D. et al., "Neutralization Of Streptococcal Pyrogenic Exotoxins And Straphylococcal Enterotoxins By Antiserum To Synthetic Peptides Representing Conserved Amino Acid Motifs", Adv. Exp. Med. Biol. 418:903–907 (1997); (published May 1997 in U.S. and Sep. 1997 in Britain according to the publisher's (*Plenum Press*, New York) catalog at http://www.plenum.com/title.cgi?0306456036).

Copy of Slides from oral presentation by Dr. Jason Bannan at "XIII Lancefield International Symposium on Streptococci and Streptococcal Diseases, Paris, France, Sep. 16, 1996 to Sep. 20, 1996".

| TOXIN | REGION 1 | | REGION 2 | |
|---|---|---|---|---|
| PEPs: | CMYGGVTEHEGN | | KKNVTVQELDYKIRKYLVDNKKLY | |
| SEA | 130 CMYGGVTLHDNN | 141 | 171 KKNVTVQELDLQARRYLQEKYNLY | 194 |
| SEB | 140 CMYGGVTEHNGN | 151 | 179 KKKVTAQELDYLTRHYLVKNKKLY | 202 |
| SEC | 137 CMYGGITKHEGN | 148 | 178 KKSVTAQELDIKARNFLINKKNLY | 201 |
| SED | 131 CTYGGVTPHEGN | 142 | 172 KKNVTVQELDAQARRYLQKDLKLY | 195 |
| SEE | 130 CMYGGVTLHDNN | 141 | 171 KKEVTVQELDLQARHYLHGKFGLY | 194 |
| SEH | 116 CLYGGITL.NSE | 126 | 151 KKNVTLQELDIKIRKILSDKYKIY | 174 |
| SPEA | 128 CIYGGVTNHEGN | 139 | 167 KKMVTAQELDYKVRKYLTDNKQLY | 190 |
| SPEC | 112 YIYGGITPAQNN | 123 | 151 KDIVTFQEIDFKIRKLYMDNYKIY | 174 |
| SSA | 134 CMYGGVTEHHRN | 145 | 174 KKQVTVQELDCKTRKILVSRKNLY | 197 |
| TSST1 | | | 161 KKQLAISTLDFEIRHQLTQIHGLY | 184 |

FIG. 1

SEQUENCE LISTING (1) GENERAL INFORMATION:

(iii) NUMBER OF SEQUENCES: 31

(2) INFORMATION FOR SEQ ID NO: 1:

(i) SEQUENCE CHARACTERISTICS:
       (A) LENGTH: 10
       (B) TYPE: AMINO ACID
       (C) STRANDEDNESS: UNKNOWN
       (D) TOPOLOGY: UNKNOWN (ii) MOLECULE TYPE: PEPTIDE (xi) SEQUENCE DESCRIPTION:SEQ ID NO: 1:

Tyr Gly Gly Xaa Thr Xaa Xaa Xaa Xaa Asn
                5                   10

(2) INFORMATION FOR SEQ ID NO: 2:

(i) SEQUENCE CHARACTERISTICS:
       (A) LENGTH: 24
       (B) TYPE: AMINO ACID
       (C) STRANDEDNESS: UNKNOWN
       (D) TOPOLOGY: UNKNOWN (ii) MOLECULE TYPE: PEPTIDE (xi) SEQUENCE DESCRIPTION:SEQ ID NO: 2:

Lys Xaa Xaa Xaa Xaa Xaa Xaa Xaa Xaa Asp Xaa Xaa
                5                   10

Xaa Arg Xaa Xaa Leu Xaa Xaa Xaa Xaa Xaa Xaa Tyr
        15                  20

(2) INFORMATION FOR SEQ ID NO: 3:

(i) SEQUENCE CHARACTERISTICS:
       (A) LENGTH: 12
       (B) TYPE: AMINO ACID
       (C) STRANDEDNESS: UNKNOWN
       (D) TOPOLOGY: UNKNOWN (ii) MOLECULE TYPE: PEPTIDE (xi) SEQUENCE DESCRIPTION:SEQ ID NO: 3:

Cys Met Tyr Gly Gly Val Thr Glu His Glu Gly Asn
                5                   10

(2) INFORMATION FOR SEQ ID NO: 4:

(i) SEQUENCE CHARACTERISTICS:
       (A) LENGTH: 24
       (B) TYPE: AMINO ACID
       (C) STRANDEDNESS: UNKNOWN
       (D) TOPOLOGY: UNKNOWN (ii) MOLECULE TYPE: PEPTIDE (xi) SEQUENCE DESCRIPTION:SEQ ID NO: 4:

Lys Lys Asn Val Thr Val Gln Glu Leu Asp Tyr Lys
                5                   10

Ile Arg Lys Tyr Leu Val Asp Asn Lys Lys Leu Tyr
        15                  20

(2) INFORMATION FOR SEQ ID NO: 5:

(i) SEQUENCE CHARACTERISTICS:
    (A) LENGTH: 14
    (B) TYPE: AMINO ACID
    (C) STRANDEDNESS: UNKNOWN
    (D) TOPOLOGY: UNKNOWN (ii) MOLECULE TYPE: PEPTIDE (xi) SEQUENCE DESCRIPTION:SEQ ID NO: 5:

Cys Met Tyr Gly Gly Val Thr Glu His Glu Gly Asn
                 5                  10
Gly Cys (2) INFORMATION FOR SEQ ID NO: 6:

(i) SEQUENCE CHARACTERISTICS:
        (A) LENGTH: 28
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 6:

Cys Gly Lys Lys Asn Val Thr Val Gln Glu Leu Asp
                 5                  10
Tyr Lys Ile Arg Lys Tyr Leu Val Asp Asn Lys Lys
         15                  20
Leu Tyr Gly Cys
         25

(2) INFORMATION FOR SEQ ID NO: 7:

(i) SEQUENCE CHARACTERISTICS:
        (A) LENGTH: 36
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 7:

Cys Met Tyr Gly Gly Val Thr Glu His Glu Gly Asn
                 5                  10
Lys Lys Asn Val Thr Val Gln Glu Leu Asp Tyr Lys
         15                  20
Ile Arg Lys Tyr Leu Val Asp Asn Lys Lys Leu Tyr
         25                  30              35

(2) INFORMATION FOR SEQ ID NO: 8:

(i) SEQUENCE CHARACTERISTICS:
        (A) LENGTH: 38
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 8:

Cys Met Tyr Gly Gly Val Thr Glu His Glu Gly Asn
                 5                  10
Lys Lys Asn Val Thr Val Gln Glu Leu Asp Tyr Lys
         15                  20

```
Ile Arg Lys Tyr Leu Val Asp Asn Lys Lys Leu Tyr
         25                  30                  35

Gly Cys
```

(2) INFORMATION FOR SEQ ID NO: 9:

(i) SEQUENCE CHARACTERISTICS:
        (A) LENGTH: 12
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 9:

```
Cys Met Tyr Gly Gly Val Thr Leu His Asp Asn Asn
                 5                  10
```

(2) INFORMATION FOR SEQ ID NO: 10:

(i) SEQUENCE CHARACTERISTICS:
        (A) LENGTH: 12
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 10:

```
Cys Met Tyr Gly Gly Val Thr Glu His Asn Gly Asn
                 5                  10
```

(2) INFORMATION FOR SEQ ID NO: 11:

(i) SEQUENCE CHARACTERISTICS:
        (A) LENGTH: 12
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 11:

```
Cys Met Tyr Gly Gly Ile Thr Lys His Glu Gly Asn
                 5                  10
```

(2) INFORMATION FOR SEQ ID NO: 12:

(i) SEQUENCE CHARACTERISTICS:
        (A) LENGTH: 12
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 12:

```
Cys Thr Tyr Gly Gly Val Thr Pro His Glu Gly Asn
                 5                  10
```

(2) INFORMATION FOR SEQ ID NO: 13:

(i) SEQUENCE CHARACTERISTICS:
        (A) LENGTH: 12
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 13:

Cys Met Tyr Gly Gly Val Thr Leu His Asp Asn Asn
                 5                   10

(2) INFORMATION FOR SEQ ID NO: 14:

(i) SEQUENCE CHARACTERISTICS:
        (A) LENGTH: 11
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 14:

Cys Leu Tyr Gly Gly Ile Thr Leu Asn Ser Glu
                 5                   10

(2) INFORMATION FOR SEQ ID NO: 15:

(i) SEQUENCE CHARACTERISTICS:
        (A) LENGTH: 12
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 15:

Cys Ile Tyr Gly Gly Val Thr Asn His Glu Gly Asn
                 5                   10

(2) INFORMATION FOR SEQ ID NO: 16:

(i) SEQUENCE CHARACTERISTICS:
        (A) LENGTH: 12
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 16:

Tyr Ile Tyr Gly Gly Ile Thr Pro Ala Gln Asn Asn
                 5                   10

(2) INFORMATION FOR SEQ ID NO: 17:

(i) SEQUENCE CHARACTERISTICS:
        (A) LENGTH: 12
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 17:

Cys Met Tyr Gly Gly Val Thr Glu His His Arg Asn
                 5                   10

(2) INFORMATION FOR SEQ ID NO: 18:

(i) SEQUENCE CHARACTERISTICS:
        (A) LENGTH: 24
        (B) TYPE: AMINO ACID
        (C) STRANDEDNESS: UNKNOWN
        (D) TOPOLOGY: UNKNOWN (ii) MOLECULE TYPE:  PEPTIDE (xi) SEQUENCE DESCRIPTION:  SEQ ID NO: 18:

Lys Lys Asn Val Thr Val Gln Glu Leu Asp Leu Gln
                 5                   10

Ala Arg Arg Tyr Leu Gln Glu Lys Tyr Asn Leu Tyr
            15                  20

(2) INFORMATION FOR SEQ ID NO: 19:

(i) SEQUENCE CHARACTERISTICS:
        (A) LENGTH:  24
        (B) TYPE:  AMINO ACID
        (C) STRANDEDNESS:  UNKNOWN
        (D) TOPOLOGY:  UNKNOWN (ii) MOLECULE TYPE:  PEPTIDE (xi) SEQUENCE DESCRIPTION:  SEQ ID NO: 19:

Lys Lys Lys Val Thr Ala Gln Glu Leu Asp Tyr Leu
                 5                   10

Thr Arg His Tyr Leu Val Lys Asn Lys Lys Leu Tyr
            15                  20

(2) INFORMATION FOR SEQ ID NO: 20:

(i) SEQUENCE CHARACTERISTICS:
        (A) LENGTH:  24
        (B) TYPE:  AMINO ACID
        (C) STRANDEDNESS:  UNKNOWN
        (D) TOPOLOGY:  UNKNOWN (ii) MOLECULE TYPE:  PEPTIDE (xi) SEQUENCE DESCRIPTION:  SEQ ID NO: 20:

Lys Lys Ser Val Thr Ala Gln Glu Leu Asp Ile Lys
                 5                   10

Ala Arg Asn Phe Leu Ile Asn Lys Lys Asn Leu Tyr
            15                  20

(2) INFORMATION FOR SEQ ID NO: 21:

(i) SEQUENCE CHARACTERISTICS:
        (A) LENGTH:  24
        (B) TYPE:  AMINO ACID
        (C) STRANDEDNESS:  UNKNOWN
        (D) TOPOLOGY:  UNKNOWN (ii) MOLECULE TYPE:  PEPTIDE (xi) SEQUENCE DESCRIPTION:  SEQ ID NO: 21:

Lys Lys Asn Val Thr Val Gln Glu Leu Asp Ala Gln
                 5                   10

Ala Arg Arg Tyr Leu Gln Lys Asp Leu Lys Leu Tyr
            15                  20

(2) INFORMATION FOR SEQ ID NO: 22:

(i) SEQUENCE CHARACTERISTICS:
        (A) LENGTH:  24
        (B) TYPE:  AMINO ACID
        (C) STRANDEDNESS:  UNKNOWN
        (D) TOPOLOGY:  UNKNOWN (ii) MOLECULE TYPE:  PEPTIDE (xi) SEQUENCE DESCRIPTION:  SEQ ID NO: 22:

-continued

```
Lys Lys Glu Val Thr Val Gln Glu Leu Asp Leu Gln
                 5                  10

Ala Arg His Tyr Leu His Gly Lys Phe Gly Leu Tyr
        15                  20

(2) INFORMATION FOR SEQ ID NO: 23:

(i) SEQUENCE CHARACTERISTICS:
        (A) LENGTH: 24
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 23:

Lys Lys Asn Val Thr Leu Gln Glu Leu Asp Ile Lys
                 5                  10

Ile Arg Lys Ile Leu Ser Asp Lys Tyr Lys Ile Tyr
        15                  20

(2) INFORMATION FOR SEQ ID NO: 24:

(i) SEQUENCE CHARACTERISTICS:
        (A) LENGTH: 24
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 24:

Lys Lys Met Val Thr Ala Gln Glu Leu Asp Tyr Lys
                 5                  10

Val Arg Lys Tyr Leu Thr Asp Asn Lys Gln Leu Tyr
        15                  20

(2) INFORMATION FOR SEQ ID NO: 25:

(i) SEQUENCE CHARACTERISTICS:
        (A) LENGTH: 24
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 25:

Lys Asp Ile Val Thr Phe Gln Glu Ile Asp Phe Lys
                 5                  10

Ile Arg Lys Leu Tyr Met Asp Asn Tyr Lys Ile Tyr
        15                  20

(2) INFORMATION FOR SEQ ID NO: 26:

(i) SEQUENCE CHARACTERISTICS:
        (A) LENGTH: 24
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 26:

Lys Lys Gln Val Thr Val Gln Glu Leu Asp Cys Lys
                 5                  10
```

-continued

```
Thr Arg Lys Ile Leu Val Ser Arg Lys Asn Leu Tyr
        15                  20
```

(2) INFORMATION FOR SEQ ID NO: 27:

(i) SEQUENCE CHARACTERISTICS:
        (A) LENGTH: 24
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 27:

```
Lys Lys Gln Leu Ala Ile Ser Thr Leu Asp Phe Glu
            5                   10
Ile Arg His Gln Leu Thr Gln Ile His Gly Leu Tyr
        15                  20
```

(2) INFORMATION FOR SEQ ID NO: 28:

(i) SEQUENCE CHARACTERISTICS:
        (A) LENGTH: 12
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 28:

```
Xaa Xaa Tyr Gly Gly Xaa Thr Xaa Xaa Xaa Xaa Asn
            5                   10
```

(2) INFORMATION FOR SEQ ID NO: 29:

(i) SEQUENCE CHARACTERISTICS:
        (A) LENGTH: 24
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 29:

```
Lys Xaa Xaa Xaa Xaa Xaa Xaa Xaa Xaa Asp Xaa Xaa
            5                   10
Xaa Arg Xaa Xaa Xaa Xaa Xaa Xaa Xaa Xaa Xaa Tyr
        15                  20
```

(2) INFORMATION FOR SEQ ID NO: 30:

(i) SEQUENCE CHARACTERISTICS:
        (A) LENGTH: 12
        (B) TYPE: AMINO ACID
        (C) STRANDEDNESS: UNKNOWN
        (D) TOPOLOGY: UNKNOWN (ii) MOLECULE TYPE: PEPTIDE (xi) SEQUENCE DESCRIPTION: SEQ ID NO: 30:

```
Cys Met Tyr Gly Gly Xaa Thr Xaa His Xaa Gly Asn
5                   10
```

(2) INFORMATION FOR SEQ ID NO: 31:

(i) SEQUENCE CHARACTERISTICS:
        (A) LENGTH: 24

-continued

```
    (B) TYPE:  AMINO ACID
    (C) STRANDEDNESS:  UNKNOWN
    (D) TOPOLOGY:  UNKNOWN (ii) MOLECULE TYPE:  PEPTIDE (xi) SEQUENCE DESCRIPTION:  SEQ ID NO: 31:

Lys Lys Xaa Val Thr Xaa Gln Glu Leu Asp Xaa Xaa
                 5                  10

Xaa Arg Xaa Xaa Xaa Xaa Xaa Xaa Xaa Xaa Leu Tyr
 15                  20
```

PEPTIDES USEFUL FOR REDUCING SYMPTOMS OF TOXIC SHOCK SYNDROME

FIELD OF THE INVENTION

This invention relates to compositions and methods for eliciting an immunogenic response in mammals, including responses which provide protection against, or reduce the severity, of toxic shock syndrome from bacterial infections. More particularly it relates to peptides, which may be polymeric, and carrier-conjugates thereof, derived from homologous sequences of the family of staphylococcal and streptococcal pyrogenic toxins. The peptides of the invention are useful to induce serum antibodies and may also be useful in diagnostic assays.

The invention also relates to antibodies induced by the peptides and/or carrier-conjugates and their use to prevent, treat, or protect against the toxic effects of bacterial toxins, including most, if not all, of the staphylococcal and streptococcal pyrogenic toxins. The invention also relates to compositions and methods to protect against, or ameliorate the effects of, autoimmune diseases which are associated with, or are the result of, the presence of staphylococcal or streptococcal toxins.

The invention also relates to diagnostic assays and kits to detect the presence of staphylococcal and streptococcal pyrogenic toxins, or antibodies thereto.

The invention also relates to isolated and purified nucleic acids encoding the peptides of the invention and transformed host cells containing those nucleic acids.

BACKGROUND OF THE INVENTION

The pyrogenic exotoxins of Group A streptococci and the enterotoxins of *Staphylococcus aureus*, which are also pyrogenic exotoxins, constitute a family of structurally related toxins which share similar biological activities (11, 13). The staphylococcal and streptococcal pyrogenic exotoxins also share significant amino acid homology throughout their sequences (11, 19, 40). This pyrogenic exotoxin family contains nine main toxin types, and several allelic variants (subtypes) have been described. Several studies have shown that the toxins share common motifs based on immunologic cross reactivity between the toxins (26, 27). These toxins share the ability to bind the major histocompatibility complex (MHC) molecules of infected hosts, as well as the variable beta chain of the T-cell receptor complex (TCR), causing an aberrant proliferation of specific T-cell subsets (3, 4, 12). This property of the toxins has labeled them as "superantigens" (36) since they do not interact with the MHC and TCR molecules in the manner of conventional antigens (14, 18).

These bacterial toxins cause a variety of syndromes in humans. Staphylococcal enterotoxins have been implicated in staphylococcal food poisoning (26), as well as toxic shock like syndromes (1). The gene sequences and deduced amino acid sequences of at least six staphylococcal enterotoxins ("SE"): A, B, C, D, E and H, are known, i.e., SEA, SEB, SEC, SED, SEE, and SEH (19, 23). The streptococcal pyrogenic exotoxins ("SPE") have been implicated in causing the symptoms of scarlet fever and toxic shock like syndrome (8, 20, 30). The sequences of three members of this family are known: SPEA, SPEC, and SSA (5, 23, 35).

Toxic shock syndrome toxin (TSST-1) from *S. aureus* shares similar biological activity with the enterotoxins and streptococcal pyrogenic exotoxins, however it is not as closely related structurally (2). Toxic shock syndrome can be exacerbated by the synergistic effects of TSST-1 with the enterotoxin/pyrogenic toxin family of toxins (9, 25). Gram negative bacterial endotoxin and the pyrogenic toxins can work synergistically to produce lethal toxic shock (17, 30).

"Toxic shock like syndrome" is the term previously used to describe the syndromes caused by staphyloccal and streptococcal pyrogenic bacterial exotoxins other than toxic shock syndrome toxin (TSST-1) from *S. aureus*. Currently, the term "toxic shock syndrome" is used to describe the syndromes caused by TSST-1 and the other pyrogenic exotoxins, and is the terminology used hereinafter.

SUMMARY OF THE INVENTION

The present invention relates to the identification of consensus sequences derived from two conserved regions of the staphylococcal enterotoxins and streptococcal pyrogenic toxins (hereinafter called "region 1" and "region 2") and the discovery that compositions comprising amino acid sequences based on these two conserved regions of the staphylococcal enterotoxins and streptococcal pyrogenic exotoxins are capable of inducing antibodies which react with a variety of staphylococcal and streptococcal pyrogenic exotoxins and are also capable of ameliorating or preventing diseases related to the deleterious effects of these toxins.

The invention also relates to compositions and methods for preventing and treating diseases related to the release of certain pyrogenic exotoxins from bacteria.

This invention provides amino acid sequences capable of inducing antibodies that reduce, inhibit or eliminate the deleterious effects of bacterial toxins, such as those of staphylococcus and a variety of streptococci. These antibodies may be induced by administration of a pharmaceutical composition and/or vaccine containing a composition comprising a peptide derived from one or both of the two conserved regions described herein, or a structurally and/or immunologically related antigen.

The amino acid sequences provided by this invention are sufficiently common to all members of this family of pyrogenic exotoxins to be useful for eliciting antibodies which are cross-reactive with toxins derived from various bacteria.

The amino acid sequences provided by this invention are also useful for new methods of preventing and treating symptoms associated with the bacterial release of the staphylococcal enterotoxins and the streptococcal pyrogenic exotoxins. Such methods include, for example, administering to an individual at risk of infection or developing a toxic reaction to the exotoxins at least one of the consensus amino acid sequences of this invention in an amount sufficient to elicit the production of antibodies to the exotoxins.

In a preferred embodiment of this invention, an individual at risk for developing toxic shock syndrome or an individual with symptoms of toxic shock syndrome may be treated by administering to such individual antibodies which have been generated in a mammal immunized with at least one of the compositions of this invention.

Vaccines and pharmaceutical compositions comprising at least one of the consensus amino acid sequences and a physiologically acceptable carrier and optionally an adjuvant are also part of this invention.

Another object of the invention is to provide antibodies induced by the peptides and carrier-conjugates thereof. These antibodies may be used to prevent, treat, or protect against the toxic effects of most, if not all, of the staphylococcal and streptococcal pyrogenic exotoxins. The antibodies may also be useful to protect against, or ameliorate the effects of, autoimmune diseases which are associated with, or are the result of, the presence of staphylococcal or streptococcal pyrogenic exotoxins. These antibodies are also useful in diagnostic assays and kits to detect the presence of staphylococcal and streptococcal pyrogenic exotoxins and to aid in the diagnosis of diseases related to the presence of those toxins.

Another object of the invention is to provide isolated and purified nucleic acids encoding the amino acid sequences of the invention, as well as suitable expression systems, vector components and transformed host cells containing those nucleic acids.

BRIEF DESCRIPTION OF THE DRAWINGS

FIG. 1. Comparison of the synthetic peptide sequences to conserved regions 1 and 2 of the staphylococcal enterotoxins (SEA, SEB, SEC, SED, SEE, and SEH), and streptococcal pyrogenic exotoxins (SPEA, SPEC, and SSA). Staphylococcal toxic shock syndrome toxin 1 (TSST-1) was compared with the region 2 peptide. Numbers represent the residue positions as a reference to where these regions exist in the whole toxin molecules. Sequences are from either the Swiss protein or Genbank databases under the following accession numbers. Swiss protein: SPEA, P08095; SPEC, P13380; SEA, P13163; SEB, P01552; SEC, P01553; SED, P20723; SEE, P12993. Genbank: SEH, U11702; SSA, L29565; TSST1, J02615.

DETAILED DESCRIPTION OF THE INVENTION

Figure 2:
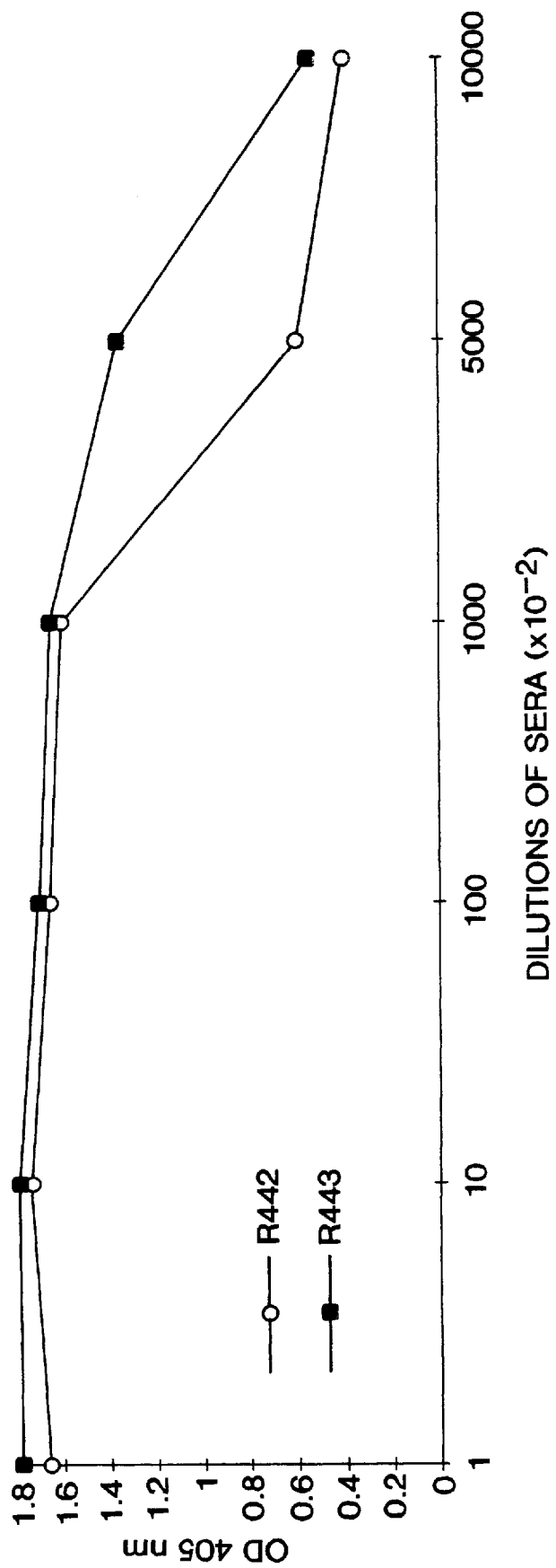
FIG. 2. ELISA titers of antibodies from rabbits immunized with polymeric peptide #6348. The peptide was diluted so that it was delivered to each well to give a final concentration of 2 $\mu$g/100 $\mu$l. The serum was then diluted to 1:1,000; 1:10,000; 1:100,000; 1:500,000; and 1:1,000,000 and 100 $\mu$l of each dilution of serum was placed in each well. Experiments were run in triplicate for each dilution of serum. Note the 1 log higher titers of rabbit #443 serum as compared to rabbit #442 serum. Cut off readings were at O.D. 0.6.

It is to be understood that both the foregoing general description and the following detailed description are exemplary and explanatory only, and are not restrictive of the invention, as claimed. The accompanying drawings, which are incorporated in and constitute a part of the specification, illustrate an embodiment of the invention and, together with the description, serve to explain the principles of the invention.

Two consensus patterns, corresponding to conserved region 1 and region 2, respectively, are identified as common to members of the staphylococcal enterotoxin and streptococcal pyrogenic toxin family of toxins when the program "Motifs" in a software package from the Genetics Computer Group, Inc. ("GCG") is run using the streptococcal SPEC toxin as an example. "Program Manual for the Wisconsin Package, Version 8, September 1994, Genetics Computer Group, 575 Science Drive, Madison, Wis., U.S.A. 53711", incorporated herein by reference.

The first consensus sequence ("GCG consensus #1") identified by the Motifs program has the amino acid sequence YGG(LIV)TXXXXN, which is rewritten herein as YGGX$_1$TX$_2$X$_3$X$_4$X$_5$N (SEQ ID NO:1), wherein X$_1$ is selected from the group consisting of L, I, or V; and X$_2$, X$_3$, X$_4$ and X$_5$ are each independently selected from the group consisting of any amino acid. This pattern is present in the staphylococcal enterotoxins and streptococcal pyrogenic exotoxins, but not in TSST-1. The second consensus sequence ("GCG consensus #2") identified by the Motifs program has the amino acid sequence KXX(LIV)XXXX (LIV)DXXXRXXLXXXXX(LIV)Y, rewritten herein as KX$_6$X$_7$X$_8$X$_9$X$_{10}$X$_{11}$X$_{12}$X$_{13}$DX$_{14}$X$_{15}$X$_{16}$RX$_{17}$X$_{18}$LX$_{19}$X$_{20}$X$_{21}$X$_{22}$X$_{23}$X$_{24}$Y (SEQ ID NO: 2), wherein X$_8$, X$_{13}$ and X$_{24}$ are each independently selected from the group consisting of L, I and V, and X$_6$, X$_7$, X$_9$, X$_{10}$, X$_{11}$, X$_{12}$, X$_{14}$, X$_{15}$, X$_{16}$, X$_{17}$, X$_{18}$, X$_{19}$, X$_{20}$, X$_{21}$, X$_{22}$ and X$_{23}$ are each independently selected from the group consisting of any amino acid. This pattern is present in the staphylococcal enterotoxins, streptococcal pyrogenic exotoxins, and TSST-1.

One object of the invention is to provide compositions comprising peptides comprising amino acid sequences based on these two conserved regions of the staphylococcal enterotoxins and streptococcal pyrogenic toxins. These peptides may be used for eliciting an immunogenic response in mammals, including responses which provide protection against, or reduce the severity, of toxic shock from staphylococcal or streptococcal infections. These peptides may also be useful to protect against, or ameliorate the effects of, autoimmune diseases which are associated with, or are the result of, the presence of staphylococcal or streptococcal pyrogenic exotoxins. These peptides are also useful in diagnostic assays and kits to detect the presence of antibodies to staphylococcal and streptococcal pyrogenic exotoxins and to aid in the diagnosis of diseases related to the presence of those toxins.

The peptides of the invention are those derived from either one or both of the following two consensus sequences: YGGX$_1$TX$_2$X$_3$X$_4$X$_5$N (SEQ ID NO:1), wherein X$_1$ is selected from the group consisting of L, I, or V; and X$_2$, X$_3$, X$_4$ and X$_5$ are each independently selected from the group consisting of any amino acid. KXX(LIV)XXXX(LIV) DXXXRXXLXXXXX(LIV)Y, rewritten herein as KX$_6$X$_7$X$_8$X$_9$X$_{10}$X$_{11}$X$_{12}$X$_{13}$DX$_{14}$X$_{15}$X$_{16}$RX$_{17}$X$_{18}$LX$_{19}$X$_{20}$X$_{21}$X$_{22}$X$_{23}$X$_{24}$Y (SEQ ID NO: 2), wherein X$_8$, X$_{13}$ and X$_{24}$ are each independently selected from the group consisting of L, I and V, and X$_6$, X$_7$, X$_9$, X$_{10}$, X$_{11}$, X$_{12}$, X$_{14}$, X$_{15}$, X$_{16}$, X$_{17}$, X$_{18}$, X$_{19}$, X$_{20}$, X$_{21}$, X$_{22}$ and X$_{23}$ are each independently selected from the group consisting of any amino acid.

A preferred consensus sequence of the invention from region 1 (consensus #1a) has the amino acid sequence X$_{25}$X$_{26}$YGGX$_1$TX$_2$X$_3$X$_4$X$_5$N (SEQ ID NO: 28), wherein X$_1$ is selected from the group consisting of L, I, and V; X$_2$, X$_4$ and X$_5$ are each independently selected from the group consisting of any amino acid; and X$_3$, X$_{25}$ and X$_{26}$ are each independently selected from the group consisting of any amino acid and of no amino acid; but preferably X$_1$ is selected from the group consisting of I and V; X$_2$ is selected from the group consisting of L, E, K, P and N; X$_3$ is selected from the group consisting of H and A and no amino acid; $X_4$ is selected from the group consisting of D, N, E, Q, and H; $X_5$ is selected from the group consisting of N, G, S, and R; $X_{25}$ is selected from the group consisting of C and Y and no amino acid; and $X_{26}$ is selected from the group consisting of M, T, L, I, and no amino acid.

A preferred consensus sequence of the invention from region 2 (consensus #2a) has the amino acid sequence: $KX_6X_7X_8X_9X_{10}X_{11}X_{12}X_{13}DX_{14}X_{15}X_{16}RX_{17}X_{18}X_{27}X_{19}X_{20}X_{21}X_{22}X_{23}X_{24}Y$ (SEQ ID NO: 29), wherein $X_8$, $X_{13}$ and $X_{24}$ are each independently selected from the group consisting of L, I and V; $X_6$, $X_7$, $X_9$, $X_{10}$, $X_{11}$, $X_{12}$, $X_{14}$, $X_{15}$, $X_{16}$, $X_{17}$, $X_{18}$ $X_{19}$, $X_{20}$, $X_{21}$, $X_{22}$, and $X_{23}$ are each independently selected from the group consisting of any amino acid; and $X_{27}$ is selected from the group consisting of L and Y; but preferably $X_6$ is selected from the group consisting of K and D; $X_7$ is selected from the group consisting of N, K, S, E, M, I and Q; $X_8$ is selected from the group consisting of L and V; $X_9$ is selected from the group consisting of T and A; $X_{10}$ is selected from the group consisting of V, A, L, F and I; $X_{11}$ is selected from the group consisting of Q and S; $X_{12}$ is selected from the group consisting of E and T; $X_{13}$ is selected from group consisting of L and I; $X_{14}$ is selected from the group consisting of L, Y, I, A, F and C; $X_{15}$ is selected from the group consisting of Q, L, K and E; $X_{16}$ is selected from the group consisting of A, T, I and V; $X_{17}$ is selected from the group consisting of R, H, N and K; $X_{18}$ is selected from the group consisting of Y, F, I, L and Q; $X_{19}$ is selected from the group consisting of Q, V, I, H, S, T and M; $X_{20}$ is selected from the group consisting of E, K, N, G, D, S and Q; $X_{21}$ is selected from the group consisting of K, N, D, R and I; $X_{22}$ is selected from the group consisting of Y, K, L, F and H; $X_{23}$ is selected from the group consisting of N, K, G and Q; $X_{24}$ is selected from the group consisting of L and I; and $X_{27}$ is L.

The following Table 1 lists the amino acids that are found at each of the variable positions in the sequences shown in FIG. 1, and the number of times they appear at that position:

TABLE 1

Frequency of the amino acids in the variable positions in the sequences shown in Figure 1

| | | | | | | | | |
|---|---|---|---|---|---|---|---|---|
| $X_1$ | 6V | 3I | | | | | | |
| $X_2$ | 3L | 2E | 1K | 2P | 1N | | | |
| $X_3$ | 7H | 1A | one deletion (no amino acid) | | | | | |
| $X_4$ | 2D | 2N | 3E | 1Q | 1H | | | |
| $X_5$ | 3N | 4G | 1S | 1R | | | | |
| $X_6$ | 9K | 1D | | | | | | |
| $X_7$ | 3N | 1K | 1S | 1E | 1M | 1I | 1Q | |
| $X_8$ | 9V | 1L | | | | | | |
| $X_9$ | 9T | 1A | | | | | | |
| $X_{10}$ | 4V | 3A | 1L | 1F | 1I | | | |
| $X_{11}$ | 9Q | 1S | | | | | | |
| $X_{12}$ | 9E | 1T | | | | | | |
| $X_{13}$ | 9L | 1I | | | | | | |
| $X_{14}$ | 2L | 2Y | 2I | 1A | 2F | 1C | | |
| $X_{15}$ | 3Q | 1L | 5K | 1E | | | | |
| $X_{16}$ | 4A | 2T | 3I | 1V | | | | |
| $X_{17}$ | 2R | 3H | 1N | 4K | | | | |
| $X_{18}$ | 5Y | 1F | 2I | 1L | 1Q | | | |
| $X_{19}$ | 2Q | 2V | 1I | 1H | 1S | 2T | 1M | |
| $X_{20}$ | 1E | 2K | 1N | 1G | 3D | 1S | 1Q | |
| $X_{21}$ | 4K | 3N | 1D | 1R | 1I | | | |
| $X_{22}$ | 3Y | 4K | 1L | 1F | 1H | | | |
| $X_{23}$ | 3N | 4K | 2G | 1Q | | | | |
| $X_{24}$ | 8L | 2I | | | | | | |
| $X_{25}$ | 8C | 1Y | | | | | | |
| $X_{26}$ | 5M | 2I | 1L | 1T | | | | |
| $X_{27}$ | 9L | 1Y | | | | | | |

In the peptides of the present invention, $X_1$, $X_8$, $X_{13}$ and $X_{24}$ may each independently be selected from the group consisting of L, I and V; $X_2$, $X_3$, $X_4$, $X_5$, $X_6$, $X_7$, $X_9$, $X_{10}$, $X_{11}$, $X_{12}$, $X_{14}$, $X_{15}$, $X_{16}$, $X_{17}$, $X_{18}$ $X_{19}$, $X_{20}$, $X_{21}$, $X_{22}$, $X_{23}$, $X_{25}$ and $X_{26}$ may each independently be any amino acid; $X_3$, $X_{25}$ and $X_{26}$ may also each independently be no amino acid; and $X_{27}$ is selected from the group consisting of L and Y. However, in general, the amino acids present at the positions $X_1$ to $X_{27}$ in the toxins shown in FIG. 1 (and listed in Table 1) are preferred for those positions, and the amino acids present most often at those positions in the toxins shown in FIG. 1 (and listed in Table 1) are more preferred. For example, from FIG. 1, and Table 1, it can be determined that H (histidine) is present in seven toxins at position $X_3$ and A (alanine) is present in one toxin at position $X_3$, and there is no amino acid present in one toxin at $X_3$. These are the preferred amino acids for position $X_3$. The more preferred amino acid for position $X_3$ in a peptide of the invention is H (histidine). The more preferred amino acids for $X_1$ through $X_{26}$ are: $X_1$=valine; $X_2$=leucine; $X_3$=histidine; $X_4$=glutamic acid; $X_5$=glycine; $X_6$=lysine; $X_7$=asparagine; $X_8$=valine; $X_9$=threonine; $X_{10}$=valine; $X_{11}$=glutamine; $X_{12}$=glutamic acid; $X_{13}$=leucine; $X_{14}$=leucine, tyrosine, isoleucine or phenylalanine; $X_{15}$=lysine; $X_{16}$=alanine; $X_{17}$=lysine; $X_{18}$=tyrosine; $X_{19}$=glutamine, valine or threonine; $X_{20}$=aspartic acid; $X_{21}$=lysine; $X_{22}$=lysine; $X_{23}$=lysine; $X_{24}$=leucine; $X_{25}$=cysteine; $X_{26}$=methionine; and $X_{27}$=leucine. But note that in the exemplified peptides of the invention described hereinbelow, i.e., SEQ ID NOS: 6, 7 and 8, inosine (I) is used at position $X_{16}$ instead of the more frequently found alanine (A).

As is evident from FIG. 1 and the above Table 1, some amino acid residues are much more highly conserved than suggested by the GCG package data provided by the "Motifs" program.

In region 1, the preferred consensus is larger (consensus #1a), and usually includes a C in the first position ($X_{25}$). The second residue ($X_{26}$) is most often a M, but this can vary. In the ninth position ($X_3$), H is the most highly conserved. The eleventh residue ($X_5$) is most often a G.

In region 2, the preferred consensus (consensus #2a) is much more highly conserved than suggested by the GCG program, especially if one excludes TSST-1 sequences from consideration, as follows: The second position ($X_6$) is more highly conserved than suggested, being almost exclusively a K; the fourth residue ($X_8$) is always a V followed exclusively by a T in the fifth position ($X_9$); the sixth position ($X_{10}$) is somewhat variable; but the seventh position ($X_{11}$) is always a Q, followed by E ($X_{12}$). The next position is almost always an L ($X_{13}$), and the second to last position ($X_{24}$) is almost always an L.

Thus, additional modified consensus sequences for region 1 and region 2, which are of narrower scope than the GCG consensus sequences #1 and #2 and the modified consensus sequences #1a and #2a, are as follows:

Consensus #1b:

$CMYGGX_1TX_2HX_4GN$ (SEQ ID NO: 30)

wherein $X_1$ is V or I, preferably V;

$X_2$ is L, E, K, P or N, preferably E or L; and $X_4$ is D, N, E, Q or H, preferably E.

Consensus #2b:

$KKX_7VTX_{10}QELDX_{14}X_{15}X_{16}RX_{17}X_{18}X_{27}X_{19}X_{20}X_{21}X_{22}X_{23}LY$ (SEQ ID NO:31)

wherein
X$_7$ is N, K, S, E, M, I or Q, preferably N;
X$_{10}$ is V, A, L, F or I, preferably V;
X$_{14}$ is L, Y, I, A, F or C, preferably Y;
X$_{15}$ is Q, L, K or E, preferably K;
X$_{16}$ is A, T, I or V, preferably I;
X$_{17}$ is R, H, N or K, preferably K;
X$_{18}$ is Y, F, I, L or Q, preferably Y;
X$_{19}$ is Q, V, I, H, S, T or M, preferably V;
X$_{20}$ is E, K, N, D, G, S or Q, preferably D;
X$_{21}$ is K, N, D, R or I, preferably N;
X$_{22}$ is Y, K, L, F or H, preferably K;
X$_{23}$ is N, K, G or Q, preferably K; and
X$_{27}$ is L or Y, preferably L.

Peptides exemplified herein are CMYGGVTEHEGN (SEQ ID NO: 3), CMYGGVTEHEGNGC* (SEQ ID NO: 5), KKNVTVQELDYKIRKYLVDNKKLY (SEQ ID NO: 4), CGKKNVTVQELDYKIRKYLVDNKKLYGC* (SEQ ID NO: 6), CMYGGVTEHEGNKKNVTVQELDYKIRKYLVDNKKLY (SEQ ID NO: 7) and CMYGGVTEHEGNKKNVTVQELDYKIRKYLVDNKKLYGC* (SEQ ID NO: 8), wherein an asterisk indicates that the peptide is a randomly cross-linked polymer. The exemplified polymer peptides are at least 6,000 to 8,000 daltons. The average size of the exemplified polymer peptides is about 12,000 to 15,000 daltons. Small peptides and/or contaminants may be removed by dialysis or other methods available in the art. Similarly, larger aggregates may be removed using, e.g., a 0.25 micron filter, which can also be used to sterilize the peptides.

Note that the amino acids cysteine and methionine, "CM", are present at the amino terminus of the exemplified region 1 peptides since those amino acids are most often found in that position in nature. Note also that the amino acids cysteine and glycine, "CG" and "GC", are used at the amino and/or carboxy-termini of some of the exemplified region 2 peptides. The amino acid cysteine "C" is used to facilitate cross-linking through the formation of disulfide bonds. The amino acid glycine, "G", is used as a spacer residue.

The preferred peptides of the invention are those which exclude full length native toxin molecules. The preferred peptides of this invention are not toxic, but toxic peptides maybe useful in this invention, for example, in eliciting antibodies in a non-human system. The most preferred peptides of the invention do not contain amino acid sequences in the sequence in which they are found in any particular native toxin molecule.

The present invention encompasses monomers of the peptides derived from either one or both of the two consensus regions described herein. These monomers may comprise one or more sequences derived from either region 1 or region 2 or both, such as consensus sequences #1 and #2, preferably consensus sequences #1a and/or #2a, more preferably consensus sequences #1b and/or #2b, most preferably one or more of the exemplified consensus sequence peptides. If the monomer contains more than one consensus sequence, these sequences may be immediately adjacent to each other or separated by a linker. In addition, different orientations of the peptides are within the scope of this invention. Furthermore, the order of the consensus peptides within the full peptide may be variable.

The present invention also encompasses homogeneous or heterogeneous polymers of the peptides disclosed herein (e.g., concatenated, cross-linked and/or fused identical peptide units or concatenated, cross-linked and/or fused diverse peptide units), and mixtures of the peptides, polymers, and/or conjugates thereof.

Linkers useful in the invention may, for example, be simply peptide bonds, or may comprise amino acids, including amino acids capable of forming disulfide bonds, but may also comprise other molecules such as, for example, polysaccharides or fragments thereof.

In the peptides exemplified herein, sequences derived from consensus region 1 and consensus region 2 may be immediately adjacent to each other, linked by peptide bonds, (see, e.g., SEQ ID NO:7) and/or connected via amino acid linkers capable of forming di-sulfide bonds via cysteine residues (see, e.g., SEQ ID NO: 8). In the native toxin molecules, the sequences of region 1 and region 2 are separated by 27 amino acids. When the linkers are additional amino acids, they are most preferably 1 to 27 amino acids in length, although longer linkers may also be used in accordance with this invention.

The linkers for use with this invention may be chosen so as to contribute their own immunogenic effect which may be either the same, or different, than that elicited by the consensus sequences of the invention. For example, such linkers may be bacterial antigens which also elicit the production of antibodies to infectious bacteria. In such instances, for example, the linker may be a protein or protein fragment of an infectious bacteria, or a bacterial polysaccharide or polysaccharide fragment.

A peptide of the invention includes any substituted analog or chemical derivative of a peptide derived from one or both of the two consensus regions described herein, most preferably of the exemplified peptides described herein, so long as the peptide is capable of either eliciting the production of antibodies capable of binding to most of the staphylococcal and streptococcal pyrogenic exotoxins, or reacting with (i.e., specifically binding to) antibodies that react with most of the staphylococcal and streptococcal pyrogenic exotoxins. Therefore, a peptide can be subject to various changes that provide for certain advantages in its use.

The peptides of the invention are useful for providing active immunization for the prevention of disease related to the deleterious effects of staphylococcal and streptococcal pyrogenic exotoxins and for preparation of antibodies as a passive immunization therapy. The peptides are designed to induce antibodies which react with a variety of staphylococcal and streptococcal pyrogenic exotoxins (preferably with at least two, more preferably with at least four, and most preferably with at least seven of the pyrogenic exotoxins) for use in therapy to increase resistance to, prevent and/or treat toxic shock syndrome. The peptides may also be useful to protect against, or ameliorate the effects of, autoimmune diseases which are associated with, or are the result of, the presence of staphylococcal or streptococcal exotoxins. The peptides of the invention will also be useful in diagnostic tests for detecting antibodies to staphylococcal and streptococcal pyrogenic exotoxins.

The peptide may be mixed with an adjuvant. The peptide also may be bound to a non-toxic non-host protein carrier to form a conjugate or it may be bound to a saccharide carrier and/or a non-toxic non-host protein carrier to form a conjugate.

The molecular weight of the peptide monomers having one consensus sequence of the invention range from about 1000 to 5000 daltons. Such lower molecular weight species of the invention may be useful as immunogens themselves or, more preferably, may be used as haptens conjugated to a larger carrier molecule, such as, for example, a protein. As with other peptides, the molecular weight of the peptide alone, when conjugated to a carrier or in the presence of an adjuvant, is related to its immunogenicity. Thus, the peptide may vary in molecular weight in order to enhance its antigenicity or immunogenicity. In an exemplified embodiment, the molecular weight of the peptide, in polymeric form, is greater than about 6000 to 8000 daltons, with an average weight of 12,000 to 15,000 daltons. The total size of the peptide is only limited to its ability to be physiologically tolerated.

The invention also relates to isolated and purified nucleic acid molecules which code for the peptides of the invention. The encoded peptides may be monomers, polymers or linked to other peptide sequences (i.e., they may be fusion proteins). Other features of the invention include vectors which comprise the nucleic acid molecules of the invention operably linked to promoters, as well as cell lines, such as prokaryotic (e.g., $E.$ $coli$) and eukaryotic (e.g., CHO and COS) cells transfected with the nucleic acid molecules of the invention. Vectors and compositions for enabling production of the peptides in vivo, i.e., in the individual to be treated or immunized, are also within the scope of this invention.

The nucleic acids encoding the peptides of the invention can be introduced into a vector such as a plasmid, cosmid, phage, virus or mini-chromosome and inserted into a host cell or organism by methods well known in the art. In general, the vectors containing these nucleic acids can be utilized in any cell, either eukaryotic or prokaryotic, including mammalian cells (e.g., human (e.g., HeLa), monkey (e.g., Cos), rabbit (e.g., rabbit reticulocytes), rat, hamster (e.g., CHO and baby hamster kidney cells) or mouse cells (e.g., L cells), plant cells, yeast cells, insect cells or bacterial cells (e.g., $E.$ $coli$). The vectors which can be utilized to clone and/or express these nucleic acids are the vectors which are capable of replicating and/or expressing the nucleic acids in the host cell in which the nucleic acids are desired to be replicated and/or expressed. See, e.g., F. Ausubel et al., *Current Protocols in Molecular Biology*, Greene Publishing Associates and Wiley-Interscience (1992) and Sambrook et al. (1989) for examples of appropriate vectors for various types of host cells. Strong promoters compatible with the host into which the gene is inserted may be used. These promoters may be inducible. The host cells containing these nucleic acids can be used to express large amounts of the protein useful in pharmaceuticals, diagnostic reagents, vaccines and therapeutics.

The nucleic acids could be used, for example, in the production of peptides for diagnostic reagents, vaccines and therapies for pyrogenic exotoxin related diseases. For example, vectors expressing high levels of peptide can be used in immunotherapy and immunoprophylaxis, after expression in humans. Such vectors include retroviral vectors and also include direct injection of DNA into muscle cells or other receptive cells, resulting in the efficient expression of the peptide, using the technology described, for example, in Wolff et al., *Science* 247:1465–1468 (1990), Wolff et al., *Human Molecular Genetics* 1(6):363–369 (1992) and Ulmer et al., *Science* 259:1745–1749 (1993).

In another embodiment of this invention antibodies are provided which react with peptides of the invention, as well as a variety of staphylococcal and streptococcal pyrogenic exotoxins (preferably with at least two, more preferably with at least four, and most preferably with at least seven of the pyrogenic exotoxins). These antibodies will be useful for passive immunization therapy to increase resistance to or prevent toxic shock syndrome or other diseases related to the presence of bacterial pyrogenic exotoxin. The antibodies may also be useful to protect against, or ameliorate the effects of, autoimmune diseases which are associated with, or are the result of, the presence of staphylococcal or streptococcal pyrogenic exotoxins. The antibodies of the invention will also be useful in diagnostic tests and kits for detecting the presence of staphylococcal and streptococcal pyrogenic exotoxins. These uses are discussed in more detail below.

Methods for Preparing Peptides of the Invention

The peptides of the invention may be prepared by synthetic methods or by recombinant DNA methods, as known in the art and as described herein.

Pharmaceutical Compositions

The pharmaceutical compositions of this invention contain an effective, immunogenic amount of peptide of this invention. The effective amount of peptide per unit dose sufficient to induce an immune response depends, among other things, on the species of mammal inoculated, the body weight of the mammal and the chosen inoculation regimen, as well as the presence or absence of an adjuvant, as is well known in the art. Inocula typically contain peptide concentrations of about 1 microgram to about 1000 micrograms per inoculation (dose), preferably about 3 micrograms to about 100 micrograms per dose, most preferably about 5 micrograms to 50 micrograms.

The term "unit dose" as it pertains to the inocula refers to physically discrete units suitable as unitary dosages for mammals, each unit containing a predetermined quantity of active material (peptide) calculated to produce the desired immunogenic effect in association with the required diluent.

Inocula are typically prepared as a solution in a physiologically acceptable carrier such as saline, phosphate-buffered saline and the like to form an aqueous pharmaceutical composition.

The route of inoculation of the peptides of the invention is typically parenteral and is preferably intramuscular, subcutaneous and the like, which results in eliciting antibodies protective against the deleterious effects of staphylococcal and streptococcal pyrogenic exotoxins. The dose is administered at least once. In order to increase the antibody level, at least one booster dose may be administered after the initial injection, preferably at about 4 to 6 weeks after the first dose. Subsequent doses may be administered as indicated.

To monitor the antibody response of individuals administered the compositions of the invention, antibody titers may be determined. In most instances it will be sufficient to assess the antibody titer in serum or plasma obtained from such an individual. Decisions as to whether to administer booster inoculations or to change the amount of the composition administered to the individual may be at least partially based on the titer.

The titer may be based on either an immunobinding assay which measures the concentration of antibodies in the serum which bind to a specific antigen, i.e. peptide or toxin; or bactericidal assays which measure the ability of the antibodies to participate with complement in killing bacteria. The ability to neutralize in vitro and in vivo biological effects of the pyrogenic exotoxins may also be assessed to determine the effectiveness of the treatment. See Example 1.

Antibodies

The term "antibodies" is used herein to refer to immunoglobulin molecules and immunologically active portions of immunoglobulin molecules. Exemplary antibody molecules are intact immunoglobulin molecules, substantially intact immunoglobulin molecules and portions of an immunoglobulin molecule, including those portions known in the art as Fab, Fab', $F(ab')_2$ and F(v) as well as chimeric antibody molecules.

An antibody of the present invention is typically produced by immunizing a mammal with an immunogen or vaccine containing one or more peptides of the invention, or a structurally and/or antigenically related molecule, to induce, in the mammal, antibody molecules having immunospecificity for the immunizing peptide or peptides. The peptide(s) or related molecule(s) may be monomeric, polymeric, conjugated to a carrier, and/or administered in the presence of an adjuvant. The antibody molecules may then be collected from the mammal if they are to be used in immunoassays or for providing passive immunity.

The antibody molecules of the present invention may be polyclonal or monoclonal. Monoclonal antibodies may be produced by methods known in the art. Portions of immunoglobulin molecules may also be produced by methods known in the art.

The antibody of the present invention may be contained in various carriers or media, including blood, plasma, serum (e.g., fractionated or unfractionated serum), hybridoma supernatants and the like. Alternatively, the antibody of the present invention is isolated to the extent desired by well known techniques such as, for example, by using DEAE Sephadex, or affinity chromatography. The antibodies may be purified so as to obtain specific classes or subclasses of antibody such as IgM, IgG, IgA, $IgG_1$, $IgG_2$, $IgG_3$, $IgG_4$ and the like. Antibody of the IgG class are preferred for purposes of passive protection.

The presence of the antibodies of the present invention, either polyclonal or monoclonal, can be determined by various assays. Assay techniques include, but are not limited to, immunobinding, immunofluorescence (IF), indirect immunofluorescence, immunoprecipitation, ELISA, agglutination and Western blot techniques.

The antibodies of the present invention have a number of diagnostic and therapeutic uses. The antibodies can be used as an in vitro diagnostic agent to test for the presence of various staphylococcal and streptococcal pyrogenic exotoxins in biological samples in standard immunoassay protocols and to aid in the diagnosis of various diseases related to the presence of bacterial pyrogenic exotoxins. Preferably, the assays which use the antibodies to detect the presence of bacterial pyrogenic exotoxins in a sample involve contacting the sample with at least one of the antibodies under conditions which will allow the formation of an immunological complex between the antibody and the toxin that may be present in the sample. The formation of an immunological complex if any, indicating the presence of the toxin in the sample, is then detected and measured by suitable means. Such assays include, but are not limited to, radioimmunoassays, (RIA), ELISA, indirect immunofluorescence assay, Western blot and the like. The antibodies may be labeled or unlabeled depending on the type of assay used. Labels which may be coupled to the antibodies include those known in the art and include, but are not limited to, enzymes, radionucleotides, fluorogenic and chromogenic substrates, cofactors, biotin/avidin, colloidal gold and magnetic particles. Modification of the antibodies allows for coupling by any known means to carrier proteins or peptides or to known supports, for example, polystyrene or polyvinyl microliter plates, glass tubes or glass beads and chromatographic supports, such as paper, cellulose and cellulose derivatives, and silica.

Such assays may be, for example, of direct format (where the labelled first antibody reacts with the antigen), an indirect format (where a labelled second antibody reacts with the first antibody), a competitive format (such as the addition of a labelled antigen), or a sandwich format (where both labelled and unlabelled antibody are utilized), as well as other formats described in the art. In one such assay, the biological sample is contacted to antibodies of the present invention and a labelled second antibody is used to detect the presence of staphylococcal and streptococcal pyrogenic exotoxins, to which the antibodies are bound.

The antibodies of the present invention are also useful as therapeutic agents in the prevention and treatment of diseases caused by the deleterious effects of staphylococcal and streptococcal pyrogenic exotoxins.

The antibodies are generally administered with a physiologically acceptable carrier or vehicle therefor. A physiologically acceptable carrier is one that does not cause an adverse physical reaction upon administration and one in which the antibodies are sufficiently soluble and retain their activity to deliver a therapeutically effective amount of the compound. The therapeutically effective amount and method of administration of the antibodies may vary based on the individual patient, the indication being treated and other criteria evident to one of ordinary skill in the art. A therapeutically effective amount of the antibodies is one sufficient to attenuate the dysfunction without causing significant side effects such as non-specific T cell lysis or organ damage. The route(s) of administration useful in a particular application are apparent to one or ordinary skill in the art.

Routes of administration of the antibodies include, but are not limited to, parenteral, and direct injection into an affected site. Parenteral routes of administration include but are not limited to intravenous, intramuscular, intraperitoneal and subcutaneous.

The present invention includes compositions of the antibodies described above, suitable for parenteral administration including, but not limited to, pharmaceutically acceptable sterile isotonic solutions. Such solutions include, but are not limited to, saline and phosphate buffered saline for intravenous, intramuscular, intraperitoneal, subcutaneous or direct injection into a joint or other area.

Antibodies for use to elicit passive immunity in humans are preferably obtained from other humans previously inoculated with compositions comprising one or more of the consensus amino acid sequences of the invention. Alternatively, antibodies derived from other species may also be used. Such antibodies used in therapeutics suffer from several drawbacks such as a limited half-life and propensity to elicit an immune response. Several methods have been proposed to overcome these drawbacks. Antibodies made by these methods are encompassed by the present invention and are included herein. One such method is the "humanizing" of non-human antibodies by cloning the gene segment encoding the antigen binding region of the antibody to the human gene segments encoding the remainder of the antibody. Only the binding region of the antibody is thus recognized as foreign and is much less likely to cause an immune response. An article describing such antibodies is Reichmann et al., "Reshaping Human Antibodies for Therapy", Nature 332:323–327 (1988), which is incorporated herein by reference.

In providing the antibodies of the present invention to a recipient mammal, preferably a human, the dosage of administered antibodies will vary depending upon such factors as the mammal's age, weight, height, sex, general medical condition, previous medical history and the like.

In general, it is desirable to provide the recipient with a dosage of antibodies which is in the range of from about 5 mg/kg to about 20 mg/kg body weight of the mammal, although a lower or higher dose may be administered. In general, the antibodies will be administered intravenously (IV) or intramuscularly (IM).

The antibodies of the present invention are intended to be provided to the recipient subject in an amount sufficient to prevent, or attenuate the severity, extent or duration of the deleterious effects of staphylococcal and streptococcal pyrogenic exotoxins.

The administration of the agents including peptide and antibody compositions of the invention may be for either "prophylactic" or "therapeutic" purpose. When provided prophylactically, the agents are provided in advance of any symptom. The prophylactic administration of the agent serves to prevent or ameliorate any subsequent deleterious effects of staphylococcal and streptococcal pyrogenic exotoxins. When provided therapeutically, the agent is provided at (or shortly after) the onset of a symptom of infection with bacteria expressing staphylococcal or streptococcal pyrogenic exotoxins. The agent of the present invention may, thus, be provided either prior to the anticipated exposure to bacteria expressing staphylococcal or streptococcal pyrogenic exotoxin (so as to attenuate the anticipated severity, duration or extent of disease symptoms) or after the initiation of the infection.

Also envisioned are therapies based upon vectors, such as viral vectors containing nucleic acid sequences coding for the peptides described herein. These molecules, developed so that they do not provoke a pathological effect, will stimulate the immune system to respond to the peptides.

1. GCG Consensus #1   YGGX$_1$TX$_2$X$_3$X$_4$X$_5$N                                              (SEQ ID NO:1)

peptide #1         CMYGGVTEHEGN                                                    (SEQ ID NO:3)

2. GCG Consensus #2   KX$_6$X$_7$X$_8$X$_9$X$_{10}$X$_{11}$X$_{12}$X$_{13}$DX$_{14}$X$_{15}$X$_{16}$RX$_{17}$X$_{18}$LX$_{19}$X$_{20}$X$_{21}$X$_{22}$X$_{23}$X$_{24}$Y   (SEQ ID NO:2)

peptide #2         KKNVTVQELDTYKIRKYLVDNKKLY                                       (SEQ ID NO:4)

For all therapeutic, prophylactic and diagnostic uses, the peptide of the invention, alone or linked to a carrier, as well as antibodies and other necessary reagents and appropriate devices and accessories may be provided in kit form so as to be readily available and easily used.

Where immunoassays are involved, such kits may contain a solid support, such as a membrane (e.g., nitrocellulose), a bead, sphere, test tube, rod, and so forth, to which a receptor such as an antibody specific for the target molecule will bind. Such kits can also include a second receptor, such as a labelled antibody. Such kits can be used for sandwich assays to detect toxins. Kits for competitive assays are also envisioned.

The following examples-illustrate certain embodiments of the present invention, but should not be construed as limiting its scope in any way. Certain modifications and variations will be apparent to those skilled in the art from the teachings of the foregoing disclosure and the following examples, and these are intended to be encompassed by the spirit and scope of the invention.

EXAMPLE 1

Peptides whose sequences are based on the two highly conserved regions of the staphylococcal and streptococcal pyrogenic exotoxins described herein were constructed. The sequences were based on alignments of the streptococcal pyrogenic exotoxins with the staphylococcal enterotoxins, and the amino acids used in positions with possible degeneracy were the amino acids most frequently found in these positions. Three of the peptides were then concatenated and polymerized to produce peptides of greater than 8000 daltons (i.e., peptides 6343, 6345 and 6348, described below). As described further below, peptide 6348 was used to immunize rabbits, which produced high titer antibodies to this peptide. These antibodies were tested for the ability to recognize the streptococcal and staphylococcal pyrogenic exotoxins. Immunological assays (immunoblots) revealed that these antibodies recognized regions common to all the pyrogenic exotoxins. These antibodies were also tested for the ability to neutralize in vitro and in vivo biological activity of the pyrogenic exotoxins. These antibodies protected against the biological T-cell proliferation of these toxins in an in vitro blastogenesis assay using human mononuclear cell populations. The lethal effects of staphylococcal toxin SEB and streptococcal pyrogenic toxin SPEA in vivo were also completely blocked by mixing the antibodies with the toxin prior to injection.

Materials and Methods

Construction of Synthetic Peptides

Peptides were constructed by solid phase synthesis (20) using the modifications described by Houghton (10).

As is evident above, synthetic peptides #1 and #2 are not native peptides, i.e., their sequences differ from those found in native toxins. Variations of these peptides have also been constructed in order to generate concatenated polymers of the peptides. These polymers were constructed by the addition of glycine and of additional cysteine residues to the amino- and/or carboxyl-termini of the initial 2 peptides, thus facilitating concatenation via disulfide bond formation (37, 38, 39). The polymerized molecules were then dialyzed to remove molecules with molecular weights less than 6000–8000 daltons. One polymeric construct is composed of the monomer:

CMYGGVTEHEGNGC (SEQ ID NO:5). An additional polymer is composed of the peptide:

CGKKNVTVQELDYKIRKYLVDNKKLYGC (SEQ ID NO:6).

In the native toxin molecules, consensus region #1 precedes consensus region #2 by 27 amino acid residues (e.g. [consensus region 1] x27 [consensus region 2]). We have constructed the peptide:

CMYGGVTEHEGNKKNVTVQELDYKIRKY-LVDNKKLY (SEQ ID NO:7). Like the native toxin molecule, this peptide is representative of the two consensus regions joined together in the proper order (region 1 in the N terminal half, and region 2 in the C-terminal half of the molecule), however they are not operated by an additional 27 residues as they are in the native toxins. We have also constructed concatenated polymers based on the monomer:

CMYGGVTEHEGNKKNVTVQELDYKIRKY-LVDNKKLYGC (SEQ ID NO:8).

| ID# | Peptide | |
|---|---|---|
| 6343 | CMYGGVTEHEGN | (SEQ ID NO:3) |
| 6344 | CMYGGVTEHEGNGC* | (SEQ ID NO:5) |
| 6345 | KKNVTVQELDYKIRKYLVDNKKLY | (SEQ ID NO:4) |
| 6346 | CGKKNVTVQELDYKIRKYLVDNKKLYGC* | (SEQ ID NO:6) |
| 6347 | CMYGGVTEHEGNKKNVTVQELDYKIRKYLVDNKKLY | (SEQ ID NO:7) |
| 6348 | CMYGGVTEHEGNKKNVTVQELDYKIRKYLVDNKKLYGC* | (SEQ ID NO:8) |

Peptides with an (*) are cross-linked polymers composed of the described sequence. It is expected that monomers of these peptides will also be useful in the present invention.

Generation of Anti-Peptide Sera

New Zealand White rabbits were immunized by subcutaneous injection with 500 μg of peptide in complete Freund's adjuvant. Additional booster injections of 500 μg in incomplete adjuvant was administered 4 weeks after the primary injections. Ten days after booster injections, the rabbits were bled, and the anti peptide titers we re determined by ELISA.

Staphylococcal enterotoxins, TSST-1, and streptococcal pyrogenic exotoxins were purchased from Toxin Technology Inc. (Sarasota, Fla.).

Immunoblots

Each of the staphylococcal and streptococcal pyrogenic exotoxins were electrophoresed through 10% SDS PAGE gels (16) and transferred to nitrocellulose for western blots (33). The western blots were developed using the rabbit anti-peptide 6348 serum (anti-pep 6348 or AP6348) diluted 1:5000, followed by goat anti-rabbit (IgG) alkaline phosphate conjugate (Sigma).

Inhibition of Blastogenesis

Human peripheral blood mononuclear cell (PBMC) preparations were stimulated by each of the staphylococcal enterotoxins and streptococcal pyrogenic exotoxins. 100 ng of toxin was used to stimulate PBMC preparations at cell concentrations of $10^5$ cells per well in 96 well microliter plates. Phytohemagglutinin (PHA) was used in place of the toxins as a positive mitogenic control. Cell culture medium was supplemented with either 10% normal rabbit serum (NRS) or AP6348 serum. Blastogenesis was assayed by incorporation of tritiated thymidine after 5 days of culture (22). All experiments were performed in triplicate.

Passive Protection of Rabbits

Female New Zealand White rabbits >1 yr old were obtained from Hazelton Dutchland Labs, Inc. (Denver, Pa.). Rabbits were challenged with staphylococcal or streptococcal toxins at doses ranging from 50 to 100 μg/kg, as previously described (24). Briefly, pyrogenic toxins were incubated with normal rabbit serum or anti-pep #6348 serum for one hour prior to challenge. Toxin-serum mixtures were administered intravenously through the marginal ear veins. Normal control rabbits were treated in an identical manner, with isotonic saline substituted for the pyrogenic toxin. Four hours later, rabbits were given a sub-lethal dose (5 μg/kg) of endotoxin (E. coli LPS, List Biological Laboratories, Inc., Campbell, Calif.). Rabbits were monitored 72 h for clinical signs of toxic shock. These included elevated temperature, diarrhea, cardiopulmonary distress, and conjunctival injection. Rabbits with severe toxic shock exhibiting cyanosis and temperatures less than 97° F. were declared moribund. Moribund rabbits were euthanized by administration of 5 ml pentobarbital sodium. All animal protocols were reviewed by the Laboratory Animal Research Center at the Rockefeller University.

Results

ELISA Assays

As seen in FIG. 2, rabbits raised significant antibody titers to peptide 6348. Similarly, rabbits receiving immunizations with peptides 6344 and 6346 also developed high titers.

Recognition of Staphylococcal and Streptococcal Toxins by Anti-Pep 6348 Serum

Figure 3:
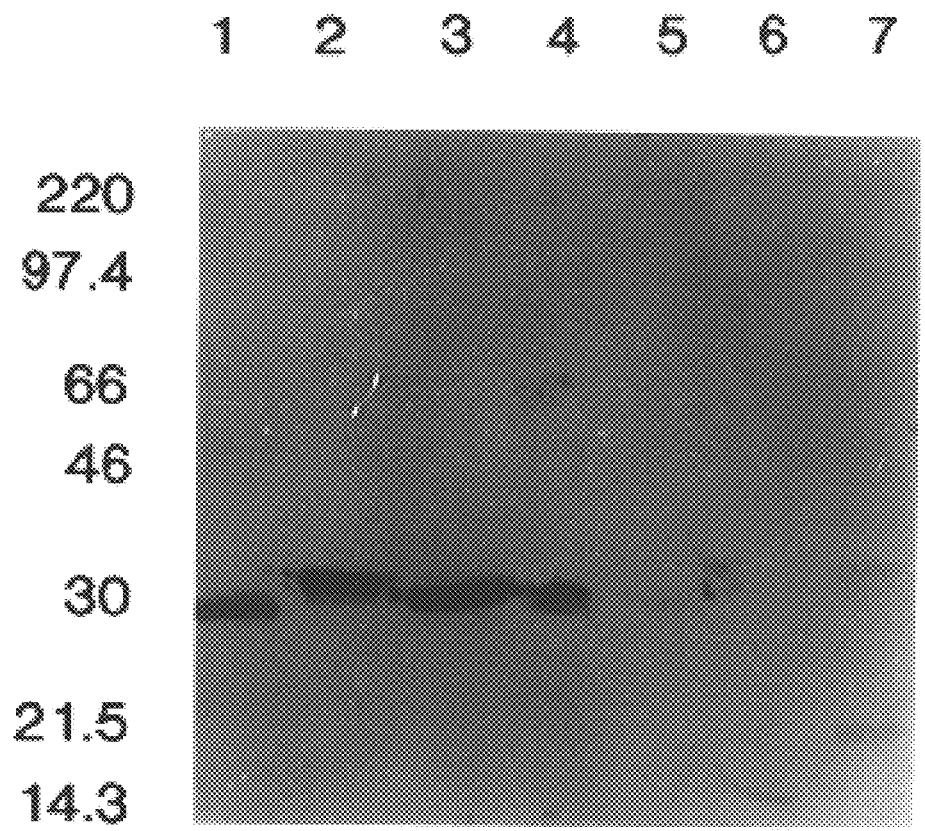
FIG. 3. 12% SDS PAGE gel immunobolt of a variety of staphylococcal and streptococcal toxins developed with the anti-peptide 6348 antibody. Note bands of correct molecular weight (M.W.) of each toxin identified by the anti-peptide antibody. Lane 1: SPEA, lane 2: SEA, lane 3: SEB, lane 4: SED, lane 5: SEE, lane 6: SEC and lane 7 TssT-1. Note bands at appropriate M.W. in lanes 1–4. Fainter bands are seen in lanes 5 and 7.

Western blots of the staphylococcal and streptococcal toxins were developed with anti-peptide 6348 serum followed by an anti-rabbit IgG alkaline phosphatase conjugate (Sigma). The results indicate the anti-peptide 6348 serum recognizes the conserved regions of the bacterial toxin molecules; SEA, SEB, SED, SEE, SPEA, and TSST-1 (FIG. 3). SEC did not show a significant reaction with anti-peptide 6348.

Blastogenesis Inhibition

Figure 4:
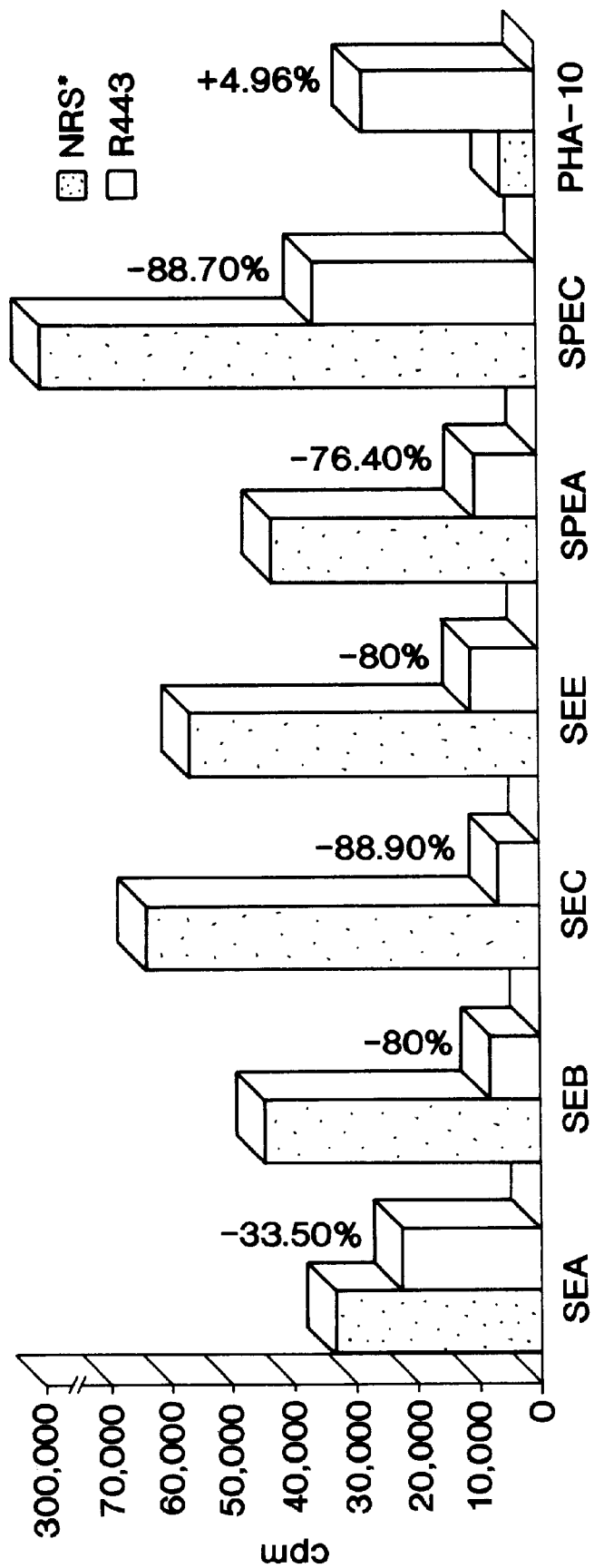
FIG. 4. Bar graphs of blastogenesis assays of human mononuclear cell populations stimulated by various toxins in the presence of normal rabbit serum and anti-peptide 6348 serum. Note the marked inhibition of SEB, SEC, SEE, SPEA and SPEC by the anti-peptide antibody. Less, but definite, inhibition of SEA by the anti-peptide antibody was also seen.

The percentage of inhibition, of toxin mediated blastogenesis, by AP6348 was assayed. Tritiated thymidine incorporation by human PBMC stimulated with staphylococcal and streptococcal pyrogenic toxins was significantly inhibited by the addition of AP6348 compared to normal rabbit serum (NRS) (FIG. 4). This suggests blastogenesis of PBMC in response to the toxins was inhibited by AP6348. The AP6348 serum did not affect the blastogenesis of human PBMC in response to PHA, suggesting a specific inhibition of toxin biologic activity.

In Vivo Protection of Rabbits

We tested the ability of AP6348 serum to prevent severe toxic shock in rabbits challenged with SEB and NRS. Rabbits challenged intravenously with a mixture of SEB and NRS developed symptoms of severe toxic shock (Table 2). One rabbit receiving 50 μg/kg SEB with NRS, and two receiving 100 μg/kg of SEB with NRS, developed severe toxic shock and were declared moribund within 30 hrs. In contrast, two rabbits challenged with 50 μg/kg and 100 μg/kg SEB with AP6348 developed fever, but this returned to normal by 32 hours. No diarrhea or cardiopulmonary depression was observed. Rabbits were followed for a total of 5 days (data not shown) and appeared fully recovered.

TABLE 2

Passive Protection of Rabbits Challenged with SEB, SPEA and LPS

| Toxin μg/kg\Serum | LPS μg/kg | Diarrhea | Temperature °F. | | | | |
|---|---|---|---|---|---|---|---|
| | | | 0 hr | 4 hr | 24 hr | 32 hr | 48 hr |
| SEB | | | | | | | |
| ns$^f$\NRS | 5 | − | 100.4 | 102 | 101.4 | 101.2 | NT |
| 50\NRS | 5 | + | 101 | 104.4 | 102.8 | 96 ◊ | |
| 100\NRS | 5 | + | 102 | 104.6 | 103 | 97 ◊ | |
| 100\NRS | 5 | + | 101 | 104.5 | 102.6 | 97 ◊ | |
| 50\APS | 5 | − | 101.4 | 103.8 | 103 | 102 | 101 |
| 100\APS | 5 | − | 100.4 | 104.4 | 103 | 102 | 101 |
| SPEA | | | | | | | |
| 50\NRS | 5 | + | 101 | 104.2 | NT ◊ | | |
| 100\NRS | 5 | + | 102 | 104.8 | NT ◊ | | |
| 50\APS | 5 | − | 102 | 104 | 103 | 102 | 102 |
| 100\APS | 5 | + | 101.6 | 104.4 | 104 | 100 | 97 ◊ | ns$^f$ = control rabbit given isotonic saline in place of SEB or SPEA
NRS = Normal rabbit serum
APS = Anti-peptide 6348 serum
◊ = animals were declared moribund
NT = not taken

Discussion

Our results demonstrate that antibodies rabbit antiserum generated to peptides representative of two regions with highly conserved amino acid sequences (AP6348) are capable of recognizing most of the staphylococcal enterotoxins and streptococcal pyrogenic exotoxins (e.g. SEA, SEB, SEC, SEE, SPEA, SPEC), as well as TSST-1, using Western blots. We expect that other, more sensitive assays, will result in the demonstration of binding of these antibodies to additional members, probably all members, of the staphylococcal and streptococcal pyrogenic toxin family.

Since recognition of the toxins by AP6348 was successful, we tested this serum for the ability to inhibit the biological effects of these pyrogenic toxins. AP6348 was capable of inhibiting in vitro blastogenesis of human PBMCs by many of the pyrogenic toxins (e.g., SEA, SEB, SEC, SEE, SPEA, and SPEC).

AP6348 was also able to provide passive in vivo protection of animals challenged with lethal doses of SEB and SPEA. These animals developed fever, however the fever returned to normal within 30 hours and remained normal. Rabbits appeared to be fully recovered within days of challenge.

In contrast, rabbits receiving similar doses of SEB and SPEA pre-incubated with NRS developed severe toxic shock, as evidenced by high fevers, diarrhea, and cardiopulmonary distress. The illness progressed and these animals were declared moribund.

The therapeutic and biological implications of these observations are as follows: (i) antibodies prepared against this peptide may be administered during the early stages of toxic shock irrespective of the toxin causing the symptoms and (ii) the peptide may be used as an immunogen to block the toxic effects of this family of superantigens.

REFERENCES

1. Bergdoll, M. S. 1985. The staphylococcal enterotoxins-an update., 247–254. In J. Jeljaszewicz (ed.). The staphylococci. Gustav Fischer Verlag, New York, N.Y.

2. Blomster-Hautamaa, D. A., B. N. Kreiswirth, J. S. Kornblum, R. P. Novick and P. M. Schlievert. 1986. The nucleotide and partial amino acid sequence of toxic shock syndrome toxin-1. Journal of Biological Chemistry. 261:15783–15786.

3. Choi, Y., B. Kotzin, L. Herron, J. Callahan, P. Marrack and J. Kappler. 1989. Interaction of staphylococcus aureus toxin superantigens with human T cells. Proc. Natl. Acad. Sci. U.S.A. 86:8941.

4. Fleischer, B. and H. Schrezenmeier. 1988. T cell stimulation by staphylococcal enterotoxins. Clonally variable response and requirement for major histocompatibility complex class II molecules on accessory or target cells. Journal of Experimental Medicine. 167:1697.

5. Goshorn, S. C. and P. M. Schlievert. 1988. Nucleotide sequence of streptococcal exotoxin type C. Infect. Immun. 56:2518–2520.

6. Grossman, D., M. Van, J. A. Mollick, S. K. Highlander and R. R. Rich. 1991. Mutation of the disulfide loop in staphylococcal enterotoxin A. Consequences for T cell recognition. J. Immunol. 147:3274–3281.

7. Hartwig, U. F. and B. Fleisher. 1993. Mutations affecting MHC class II binding of the superantigen streptococcal erythrogenic toxin A. International Immunology. 5:869–875.

8. Hauser, A. R., D. L. Stevens, E. L. Kaplan and P. M. Schlievert. 1991. Molecular analysis of pyrogenic exotoxins from streptococcus pyogenes isolates associated with toxic shock-like syndrome. Journal of Clinical Microbiology. 29:1562–1567.

9. Hensler, T., M. Köller, C. Geoffroy, J. E. Alouf and W. König. 1993. *Staphylococcus aureus* toxic shock syndrome toxin 1 and streptococcus pyogenes erythrogenic toxin A modulate inflammatory mediator release from human neutrophils. Infect. Immun. 61:1055–1061.

10. Houghten, R. A. 1985. General method for the rapid solid phase synthesis of large numbers of peptides: specificity of antigen-antibody interactions at the level of individual amino acids. Proc. Natl. Acad. Sci. USA. 82:5131–5135.

11. Hynes, W. L., C. R. Weeks, J. J. Iandolo and J. J. Ferretti. 1987. Immunologic cross-reactivity of type A streptococcal exotoxin (erythrogenic toxin) and staphylococcal enterotoxins B and C1. Infect. Immun. 55:837–840.

12. Janeway, C. A. J., J. Yagi, P. J. Conrad, M. E. Katz, B. Jones, S. Vroegop and S. Buxser. 1989. T-cell responses to Mls and to bacterial proteins that mimic its behavior. Immunology Reviews. 107:61.

13. Johnson, L. P., J. J. L'Italien and P. M. Schlievert. 1986. Streptococcal pyrogenic exotoxin type A (scarlet fever toxin) is related to *Staphylococcus aureus* enterotoxin B. Molecular and General Genetics. 203:354–356.

14. Kappler, J., B. L. Kotzin, L. Herron, E. W. Gelfand, R. D. Bigler, A. Boylston, S. Carrell, D. N. Posnett, Y. Choi and P. Marrack. 1989. Vβ-specific stimulation of human T-cells by staphylococcal toxins. Science. 248:705.

15. Kappler, J. W., A. Herman, J. Clements and P. Marrack. 1992. Mutations defining functional regions of the superantigen staphylococcal enterotoxin B. Journal of Experimental Medicine. 175:387–396.

16. Laemmli, U. K. 1970. Cleavage of structural proteins during the assembly of the head of bacteriophage T4. Nature. 227:680.

17. Leonard, B. A. and P. M. Schlievert. 1992. Immune cell lethality induced by streptococcal pyrogenic exotoxin A and endotoxin. Infect. Immun. 60:3747–3755.

18. Marrack, P., M. Blackman, E. Kushnir and J. Kappler. 1990. The toxicity of staphylococcal enterotoxin B in mice is mediated by T cells. Journal of Experimental Medicine. 171:455.

19. Marrack, P. and J. Kappler. 1990. The staphylococcal enterotoxins and their relatives. Science. 248:705–711.

20. Merrifield, R. B. 1963. Solid-phase peptide synthesis I. The synthesis of a tetrapeptide. J. Am. Chem. Soc. 85:2149–2154.

21. Musser, J. M., A. R. Hauser, M. H. Kim, P. M. Schlievert, K. Nelson and R. K. Selander. 1991. Streptococcus pyogenes causing toxic-shock-like syndrome and other invasive diseases: clonal diversity and pyrogenic exotoxin expression. Proceedings of the National Academy of Sciences of the United States of America. 88:2668–2672.

22. Read, S. E., H. F. M. Reid, V. A. Fischetti, T. Poon-King, R. Ramkissoon, M. McDowell and J. B. Zabriskie. 1986. Serial studies on the cellular immune response to streptococcal antigens in acute and convalescent rheumatic fever patients in Trinidad. Journal of Clinical Immunology. 6:433–441.

23. Reda, K. B., V. Kapur, J. A. Mollick, J. G. Lamphear, J. M. Musser and R. R. Rich. 1994. Molecular characterization and phylogenetic distribution of the streptococcal superantigen gene (ssa) from streptococcus pyogenes. Infect. Immun. 62:1867–1874.

24. Ren, K., J. D. Bannan, V. Pancholi, A. L. Cheung, J. C. Robbins, V. A. Fischetti and J. B. Zabriskie. 1994. Characterization and biological properties of a new staphylococcal exotoxin. Journal of Experimental Medicine. 180:1675–1683.

25. Smith, R. J., P. M. Schlievert, I. M. Himelright and L. M. Baddour. 1994. Dual infections with staphylococcus aureus and streptococcus pyogenes causing toxic shock syndrome. Possible synergistic effects of toxic shock syndrome toxin 1 and streptococcal pyrogenic exotoxin C. Diagnostic Microbiology & Infectious Disease. 19:245–247.

26. Spero, L., B. Morlock and J. Metzger. 1978. On the cross-reactivity of staphylococcal enterotoxins A, B, and C. J. Immunol. 120:86–89.

27. Spero, L. and B. A. Morlock. 1978. Biological activities of the peptides of staphylococcal enterotoxin C formed by limited tryptic hydrolysis. Journal of Biological Chemistry. 253:8787–8791.

28. Spero, L. and B. A. Morlock. 1979. Cross-reactions between tryptic polypeptides of staphylococcal enterotoxins B and C. J. Immunol. 122:1285–1289.

29. Stelma, G. N., Jr. and M. S. Bergdoll. 1982. Inactivation of staphylococcal enterotoxin A by chemical modification. Biochemical and Biophysical Research Communications. 105:121–126.

30. Stevens, D. L., M. H. Tanner, J. Winship, R. Swarts, K. M. Ries, P. M. Schlievert and E. Kaplan. 1989. Severe group A streptococcal infections associated with a toxic shock-like syndrome and scarlet fever toxin A. The New England Journal of Medicine. 321:1–7.

31. Sugiyama, H., E. M. J. McKissic, M. S. Bergdoll and B. Heller. 1964. Enhancement of bacterial endotoxin lethality by staphylococcal enterotoxin. J. Infect. Dis. 114:111–118.

32. Swaminathan, S., W. Furey, J. Pletcher and M. Sax. 1992. Crystal structure of staphylococcal enterotoxin B, a superantigen. Nature. 359:801–806.

33. Towbin, H., T. Staehlin and J. Gordon. 1979. Electrophoretic transfer of proteins from polyacrylamide gels to nitrocellulose sheets. Procedure and some applications. Proceedings of the National Academy of Sciences, U.S.A. 76:4350.

34. Van den Bussche, R. A., J. D. Lyon and G. A. Bohac. 1993. Molecular evolution of the staphylococcal and streptococcal pyrogenic toxin gene family. Molecular Phylogenetics and Evolution. 2:281–292.

35. Weeks, C. R. and J. J. Ferretti. 1986. Nucleotide sequence of the type A streptococcal exotoxin (erythrogenic toxin) gene from streptococcus pyogenes bacteriophage T12. Infect. Immun. 52:144–150.

36. White, J., A. Herman, A. M. Pullen, R. Kubo, J. W. Kappler and P. Marrack. 1989. The V beta-specific superantigen staphylococcal enterotoxin B: stimulation of mature T cells and clonal deletion in neonatal mice. Cell. 56:27–35.

37. Patarroyo, M.E., R. Amador, P. Clavijo, A. Moreno, F. Guzman, P. Romero, R. Tascon, A. Franco, L. A. Murillo, G. Ponton and G. Trujillo. 1988. A synthetic vaccine protects humans against challenge with Plasmodium falciparum malaria. Nature. 332:158–161.

38. Lopez, M. C., Y. Silva, M. C. Thomas, A. Garcia, M. J. Faus, P. Alonso, F. Martinez, G. Del Real and C. Alonso. 1994. Characterization of SPf(66)n: a chimeric molecule used as a malaria vaccine. Vaccine. 12:585–591.

39. Rodriguez, R., A. Moreno, F. Guzman, M. Calvo and M. E. Patarroyo. 1990. Studies in owl monkeys leading to the development of a synthetic vaccine against the asexual blood stages of Plasmodium falciparum. Am. J. Trop. Med. Hyg. 43:339–354.

40. Hoffman, M. L., L. M. Jablonski, K.K. Crum, S. P. Hackett, Y.-I. Chi, C. V. Stauffacher, D. L. Stevens and G. A. Bohach. 1994. Predictions of T-cell receptor and Major Histocompatibility Complex-binding sites on staphylococcal enterotoxin C1. Infection and Immunity. 62:3396–3407.

Modifications of the above described modes for carrying out the invention that are obvious to those of skill in the fields of immunology, protein chemistry, microbiology, medicine, and related fields are intended to be within the scope of the following claims.

Every reference cited hereinbefore is hereby incorporated by reference in its entirety.

The following table shows the correspondence between peptides in FIG. 1 and their sequence identification numbers:

TABLE 3

Correspondence between Sequence Indentification Numbers and Peptides in FIG. 1

| | FIG. 1 | Sequence ID Nos. |
|---|---|---|
| | Region 1 | |
| PEP | CMYGGVTEHEGN | SEQ ID NO:3 |
| SEA | 130 CMYGGCTLHDNN 141 | SEQ ID NO:9 |
| SEB | 140 CMYGGVTEHNGN 151 | SEQ ID NO:10 |

TABLE 3-continued

Correspondence between Sequence
Indentification Numbers and Peptides in FIG. 1

| | FIG. 1 | | Sequence ID Nos. |
|---|---|---|---|
| SEC | 137 CMYGGITKHEGN 148 | | SEQ ID NO:11 |
| SED | 131 CTYGGVTPHEGN 142 | | SEQ ID NO:12 |
| SEE | 130 CMYGGVTLHDNN 141 | | SEQ ID NO:13 |
| SEH | 116 CLYGGITL.NSE 126 | | SEQ ID NO:14 |
| SPEA | 128 CIYGGVTNHEGN 139 | | SEQ ID NO:15 |
| SPEC | 112 YIYGGITPAQNN 123 | | SEQ ID NO:16 |
| SSA | 134 CMYGGVTEHHRN 145 | | SEQ ID NO:17 |
| | Region 2 | | |
| PEP | KKNVTVQELDYKIRKYLVDNKKLY | | SEQ ID NO:4 |
| SEA | 171 KKNVTVQELDLQARRYLQEKYNLY 194 | | SEQ ID NO:18 |
| SEB | 179 KKKVTAQELDYLTRHYLVKNKKLY 202 | | SEQ ID NO:19 |
| SEC | 178 KKSVTAQELDIKARNFLINKKNLY 201 | | SEQ ID NO:20 |
| SED | 172 KKNVTVQELDAQARRYLQKDLKLY 195 | | SEQ ID NO:21 |
| SEE | 171 KKEVTVQELDLQARHYLHGKFGLY 194 | | SEQ ID NO:22 |
| SEH | 151 KKNVTLQELDIKIRKILSDKYKIY 174 | | SEQ ID NO:23 |
| SPEA | 167 KKMVTAQELDYKBRKYLTDNKQLY 190 | | SEQ ID NO:24 |
| SPEC | 151 KDIVTFQEIDFKIRKLYMDNYKIY 174 | | SEQ ID NO:25 |
| SSA | 174 KKQVTVQELDCKTRKILVSRKNLY 197 | | SEQ ID NO:26 |
| TSST1 | 161 KKQLAISTLDFEIRHQLTQIHGLY 184 | | SEQ ID NO:27 |

We claim:

1. A peptide comprising at least one amino acid sequence selected from the group consisting of CMYGGVTEHEGN (SEQ ID NO: 3), CMYGGVTEHEGNGC (SEQ ID NO: 5), KKNVTVQELDYKIRKYLVDNKKLY (SEQ ID NO: 4), CGKKNVTVQELDYKIRKYLVDNKKLYGC (SEQ ID NO: 6), CMYGGVTEHEGNKKNVTVQELDYKIRKYLVDNKKLY (SEQ ID NO: 7), and CMYGGVTEHEGNKKNVTVQELDYKIRKYLVDNKKLYGC (SEQ ID NO: 8).

2. The peptide of claim 1 wherein said peptide comprises the amino acid sequence CMYGGVTEHEGN (SEQ ID NO: 3).

3. The peptide of claim 1 wherein said peptide comprises the amino acid sequence KKNVTVQELDYKIRKYLVDNKKLY (SEQ ID NO: 4).

4. The peptide of claim 1 wherein said peptide comprises the amino acid sequence CMYGGVTEHEGNGC (SEQ ID NO: 5).

5. The peptide of claim 1 wherein said peptide comprises the amino acid sequence CGKKNVTVQELDYKIRKYLVDNKKLYGC (SEQ ID NO: 6).

6. The peptide of claim 1 wherein said peptide comprises the amino acid sequence CMYGGVTEHEGNKKNVTVQELDYKIRKYLVDNKKLY (SEQ ID NO: 7).

7. The peptide of claim 1 wherein said peptide comprises the amino acid sequence CMYGGVTEHEGNKKNVTVQELDYKIRKYLVDNKKLYGC (SEQ ID NO: 8).

8. The peptide of claim 1 wherein said amino acid sequence is a component of a larger molecule which is retained after dialysis to remove molecules with molecular weights of less than 6000–8000 daltons.

9. A pharmaceutical composition comprising a peptide comprising at least one amino acid sequence selected from the group consisting of CMYGGVTEHEGN (SEQ ID NO: 3), CMYGGVTEHEGNGC (SEQ ID NO: 5), KKNVTVQELDYKIRKYLVDNKKLY (SEQ ID NO: 4), CGKKNVTVQELDYKIRKYLVDNKKLYGC (SEQ ID NO: 6), CMYGGVTEHEGNKKNVTVQELDYKIRKYLVDNKKLY (SEQ ID NO: 7), and CMYGGVTEHEGNKKNVTVQELDYKIRKYLVDNKKLYGC (SEQ ID NO: 8) in a physiologically acceptable carrier.

10. The pharmaceutical composition according to claim 9 wherein said peptide comprises the amino acid sequence CMYGGVTEHEGN (SEQ ID NO: 3).

11. The pharmaceutical composition according to claim 9 wherein said peptide comprises the amino acid sequence KKNVTVQELDYKIRKYLVDNKKLY (SEQ ID NO: 4).

12. The pharmaceutical composition according to claim 9 wherein said peptide comprises the amino acid sequence CMYGGVTEHEGNGC (SEQ ID NO: 5).

13. The pharmaceutical composition according to claim 9 wherein the said peptide comprises the amino acid sequence CGKKNVTVQELDYKIRKYLVDNKKLYGC (SEQ ID NO: 6).

14. The pharmaceutical composition according to claim 9 wherein said peptide comprises the amino acid sequence CMYGGVTEHEGNKKNVTVQELDYKIRKYLVDNKKLY (SEQ ID NO: 7).

15. The pharmaceutical composition according to claim 9 wherein said peptide comprises the amino acid sequence CMYGGVTEHEGNKKNVTVQELDYKIRKYLVDNKKLYGC (SEQ ID NO: 8).

16. The pharmaceutical composition according to claim 9 wherein said amino acid sequence is a component of a larger molecule which is retained after dialysis to remove molecules with molecular weights of less than 6000–8000 daltons.

17. A method of including serum antibodies that bind at least one staphylococcal enterotoxin or streptococcal exotoxin, said method comprising administering to a mammal, in a physiologically acceptable carrier, an amount of a peptide of claim 1 sufficient to elicit production of said antibodies.

18. The method of claim 17 wherein said peptide comprises the amino acid sequence CMYGGVTEHEGN (SEQ ID NO: 3).

19. The method of claim 17 wherein said peptide comprises the amino acid sequence KKNVTVQELDYKIRKYLVDNKKLY (SEQ ID NO: 4).

20. The method of claim 17 wherein said peptide comprises the amino acid sequence CMYGGVTEHEGNGC (SEQ ID NO: 5).

21. The method of claim 17 wherein said peptide comprises the amino acid sequence CGKKNVTVQELDYKIRKYLVDNKKLYGC (SEQ ID NO: 6).

22. The method of claim 17 wherein said peptide comprises the amino acid sequence CMYGGVTEHEGNKKNVTVQELDYKIRKYLVDNKKLY (SEQ ID NO: 7).

23. The method of claim 17 wherein said peptide comprises the amino acid sequence CMYGGVTEHEGNKKNVTVQELDYKIRKYLVDNKKLYGC (SEQ ID NO: 8).

24. The peptide of claim 1 wherein said peptide further comprises a concatenated polymer.

25. The pharmaceutical composition according to claim 9 wherein said peptide further comprises a concatenated polymer.

* * * * *

UNITED STATES PATENT AND TRADEMARK OFFICE
CERTIFICATE OF CORRECTION

PATENT NO. : 6,075,119
DATED : June 13, 2000
INVENTOR(S) : Jason D. Bannan and John B. Zabriskie It is certified that error appears in the above-identified patent and that said Letters Patent is hereby corrected as shown below:

Column 15,
Line 25, "we re" should read -- were --.

Column 38,
Line 35, "including" should read -- inducing --.

Signed and Sealed this

Tenth Day of August, 2004

JON W. DUDAS
*Acting Director of the United States Patent and Trademark Office*